US008124111B2

(12) United States Patent
Saba

(10) Patent No.: US 8,124,111 B2
(45) Date of Patent: Feb. 28, 2012

(54) IMMUNOMODULATION BY ALTERING SPHINGOSINE 1-PHOSPHATE LYASE (SPL) ACTIVITY

(75) Inventor: Julie D. Saba, Oakland, CA (US)

(73) Assignee: Children's Hospital & Research Center at Oakland, Oakland, CA (US)

( * ) Notice: Subject to any disclaimer, the term of this patent is extended or adjusted under 35 U.S.C. 154(b) by 595 days.

(21) Appl. No.: 11/917,029

(22) PCT Filed: Jun. 8, 2006

(86) PCT No.: PCT/US2006/022805
§ 371 (c)(1),
(2), (4) Date: Sep. 8, 2008

(87) PCT Pub. No.: WO2006/135862
PCT Pub. Date: Dec. 21, 2006

(65) Prior Publication Data
US 2009/0202551 A1    Aug. 13, 2009

Related U.S. Application Data

(60) Provisional application No. 60/689,611, filed on Jun. 10, 2005.

(51) Int. Cl.
*A61K 39/00* (2006.01)
*C12N 9/88* (2006.01)

(52) U.S. Cl. .......................................... 424/278.1; 514/9
(58) Field of Classification Search .................. None
See application file for complete search history.

(56) References Cited

U.S. PATENT DOCUMENTS

| | | | |
|---|---|---|---|
| 5,087,617 A | 2/1992 | Smith | 514/44 |
| 5,093,246 A | 3/1992 | Cech et al. | 435/91 |
| 5,116,742 A | 5/1992 | Cech et al. | 435/91 |
| 5,135,917 A | 8/1992 | Burch | 514/44 |
| 5,144,019 A | 9/1992 | Rossi et al. | 536/27 |
| 5,168,053 A | 12/1992 | Altman et al. | 435/91 |
| 5,176,996 A | 1/1993 | Hogan et al. | 435/6 |
| 5,180,818 A | 1/1993 | Cech et al. | 536/23.1 |
| 5,190,931 A | 3/1993 | Inouye | 435/91 |
| 5,272,262 A | 12/1993 | Rossi et al. | 536/23.2 |
| 6,423,527 B1 | 7/2002 | Saba et al. | 435/232 |
| 6,495,359 B1 | 12/2002 | Saba et al. | 435/232 |
| 6,506,559 B1 | 1/2003 | Fire et al. | 435/6 |
| 6,569,666 B1 | 5/2003 | Saba | 435/232 |
| 7,041,291 B2 | 5/2006 | Saba et al. | 424/139.1 |
| 2002/0155512 A1* | 10/2002 | Liao et al. | 435/7.21 |
| 2003/0059922 A1 | 3/2003 | Saba et al. | 435/232 |
| 2003/0166897 A1 | 9/2003 | Saba et al. | 536/23.1 |
| 2003/0175939 A1 | 9/2003 | Saba et al. | 435/232 |
| 2003/0219782 A1 | 11/2003 | Saba et al. | 435/6 |
| 2004/0126834 A1 | 7/2004 | Saba | 435/19 |

FOREIGN PATENT DOCUMENTS

| | | |
|---|---|---|
| WO | 99/16888 | 4/1999 |
| WO | 99/32619 | 7/1999 |
| WO | 01/75164 | 10/2001 |
| WO | 03/062390 | 7/2003 |

OTHER PUBLICATIONS

Burt et al. Journal of Autoimmunity, 2004, vol. 10, p. 1-5.*
Fyrst et al., "Characterization of free endogenous $C_{14}$ and $C_{16}$ sphingoid bases from *Drosophila melanogaster*," *Journal of Lipid Research* 45:54-62, 2004.
Jiang et al., "γ-Tocopherol or combinations of vitamin E forms induce cell death in human prostate cancer cells by interrupting sphingolipid synthesis," *PNAS 101*(50:17825-17830, 2004.
Mailand et al., "Deregulated human Cdc14A phosphatase disrupts centrosome separation and chromosome segregation," *Nature Cell Biology* 4:317-323, 2002.
Oskouian et al., "Regulation of Sphingosine-1-phosphate Lyase Gene Expression by Members of the GATA Family of Transcription Factors," *Journal of Biological Chemistry 280*(18):18403-18410, 2005.
Reiss et al., "Sphingosine-phosphate Lyase Enhances Stress-induced Ceramide Generation and Apoptosis," *Journal of Biological Chemistry 279*(2):1281-1290, 2004.
Spiegel et al., "Sphingosine-1-phosphate: signaling inside and out," *FEBS Letters 476*:55-57, 2000.
Adams and Cory, "The Bcl-2 protein family: Arbiters of cell survival," *Science 281*:1322-1326, Aug. 28, 1998.
Agrawal and Goodchild, "Oligodeoxynucleoside methylphosphonates: Synthesis and enzymic degradation," *Tetrahedron Letters 28*(31):3539-3542, 1987.
Akdis and Blaser, "Regulation of specific immune responses by chemical and structural modifications of allergens," *International Archives of Allergy and Immunology 121*:261-269, Jun. 5, 2000.
Allende et al., "Expression of the sphingosine 1-phosphate receptor, $S1P_1$, on T-cells controls thymic emigration," *Journal of Biological Chemistry 279*(15):15396-15401, Apr. 9, 2004.
Arends et al., "Apoptosis. The role of the endonuclease," *American Journal of Pathology 136*(3):593-608, Mar. 1990.
Ashkenazi and Dixit, "Death receptors: Signaling and modulation," *Science 281*:1305-1308, Aug. 28, 1998.
Bandhuvula et al., "The immune modulator FTY720 inhibits sphingosine-1-phosphate lyase activity," *Journal of Biological Chemistry* 280(40):33697-33700, Oct. 7, 2005.

(Continued)

*Primary Examiner* — Yunsoo Kim
(74) *Attorney, Agent, or Firm* — Seed IP Law Group PLLC

(57) ABSTRACT

Compositions and methods for modulating immune function are provided based on the unexpected discovery that inhibition of sphingosine-1-phosphate lyase (SPL) activity confers useful immunosuppressive effects, for example to modulate immune function in treatment or prevention of inflammation, transplant graft rejection, autoimmune disease, allergy, or other conditions, including therapeutic alteration of immune system cell survival and/or proliferation. Altering SPL activity by direct or indirect pharmacological intervention, or alternatively by molecular genetic methods to alter SPL expression levels, are also contemplated.

7 Claims, 5 Drawing Sheets

OTHER PUBLICATIONS

Barnes, "New directions in allergic diseases: Mechanism-based anti-inflammatory therapies," *Journal of Allergy and Clinical Immunology* 106(1 Part 1):5-16, 2000.
Bass, "Double-stranded RNA as a template for gene silencing," *Cell* 101:235-238, Apr. 28, 2000.
Beach, "Immunologic versus toxicologic mechanisms in airway responses," *Occupational Medicine: State of the Art Reviews* 15(2):455-469, Apr.-Jun. 2000.
Bejaoui et al., "*SPTLC1* is mutated in hereditary sensory neuropathy, type 1," *Nature Genetics* 27:261-262, Mar. 1, 2001.
Bernstein et al., "The rest is silence," *RNA* 7:1509-1521, 2001.
Billich et al., "Phosphorylation of the Immunomodulatory Drug FTY720 by sphingosine kinases," *Journal of Biological Chemistry* 278(48):47408-47415, Nov. 28, 2003.
Brinkmann and Lynch, "FTY720: targeting G-protein-coupled receptors for sphingosine 1-phosphate in transplantation and autoimmunity," *Current Opinion in Immunology* 14(5):569-575, Oct. 2002.
Brinkmann et al., "The immune modulator FTY720 targets sphingosine 1-phosphate receptors," *Journal of Biological Chemistry* 277(24):21453-21457, Jun. 14, 2002.
Brinkmann, "FTY720: Mechanism of action and potential benefit in organ transplantation," *Yonsei Medical Journal* 45(6):991-997, 2004.
Budde et al., "First human trial of FTY720, a novel immunomodulator, in stable renal transplant patients," *Journal of the American Society of Nephrology* 13:1073-1083, 2002.
Caligan et al., "A high-performance liquid chromatographic method to measure sphingosine 1-phosphate and related compounds from sphingosine kinase assays and other biological samples," *Analytical Biochemistry* 281:36-44, 2000.
Campbell et al., "Effects of DL-α-difluoromethylornithine, 4-deoxypyridoxine and methylglyoxal bis(guanylhydrazone) on allograft prolongation," *Life Sciences* 48(3):225-235, 1991.
Carthew, "Gene silencing by double-stranded RNA," *Current Opinion in Cell Biology* 13:244-248, 2001.
Chen et al., "Identification and validation of PDGF transcriptional targets by microarray-coupled gene-trap mutagenesis," *Nature Genetics* 36(3):304-312, Mar. 2004.
Chen et al., "Chemical modification of gene silencing oligonucleotides for drug discovery and development," *Drug Discovery Today* 10(8):587-593, Apr. 2005.
Chiba et al., FTY720, a novel immunosuppressant, induces sequestration of circulating mature lymphocytes by acceleration of lymphocyte homing in rats. I. FTY720 selectively decreases the number of circulating mature lymphocytes by acceleration of lymphocyte homing, *Journal of Immunology* 160:5037-5044, 1998.
Chiba et al., "Immunosuppressive activity of FTY720, sphingosine 1-phosphate receptor agonist: I. Prevention of allograft rejection in rats and dogs by FTY720 and FTY720-phosphate," *Transplantation Proceedings* 37:102-106, 2005.
Clusel et al., "Ex vivo regulation of specific gene expression by nanomolar concentration of double-stranded dumbbell oligonucleotides," *Nucleic Acids Research* 21(15):3405-3411, 1993.
Cohen, "Caspases: the executioners of apoptosis," *Biochemical Journal* 326:1-16, 1997.
Dawkins et al., Mutations in *SPTLC1*, encoding serine palmitoyltransferase, long chain base subunit-1, cause hereditary sensory neuropathy type I, *Nature Genetics* 27:309-312, Mar. 1, 2001.
Eckstein, "Nucleoside phosphorothioates," *Annual Reviews of Biochemistry* 54:367-402, 1985.
Eckstein and Gish, "Phosphorothioates in molecular biology," *Trends in Biochemical Sciences* 14:97-100, Mar. 1989.
Elbashir et al., "Duplexes of 21-nucleotide RNAs mediate RNA interference in cultured mammalian cells," *Nature* 411:494-498, May 24, 2001.
Ellerby et al., "Establishment of a cell-free system of neuronal apoptosis: Comparison of premitochondrial, mitochondrial, and postmitochondrial phases," *Journal of Neuroscience* 17(16):6165-6178, Aug. 15, 1997.
Evan et al., "A matter of life and cell death," *Science* 281:1317-1322, Aug. 28, 1998.
Fadok et al., "Exposure of phosphatidylserine on the surface of apoptotic lymphocytes triggers specific recognition and removal by macrophages," *Journal of Immunology* 148(7):2207-2216, Apr. 1, 1992.
Fire et al., "Potent and specific genetic interference by double-stranded RNA in *Caenorhabditis elegans*," *Nature* 391:806-811, Feb. 19, 1998.
Forrest et al., "Immune cell regulation and cardiovascular effects of sphingosine 1-phosphate receptor agonists in rodents are mediated via distinct receptor subtypes," *Journal of Pharmacology and Experimental Therapeutics* 309(2):758-768, 2004.
Frydas et al., "MCP-1 and MIP-2 response in *Trichinella spiralis* infected mice treated with 4-deoxypyridoxine (4-DPD)," *Immunology Letters* 83:31-37, 2002.
Fujita et al., "Fungal metabolites. Part 11. A potent immunosuppressive activity found in *Isaria sinclairii* metabolite," *Journal of Antibiotics* 47(2):208-215, Feb. 1994.
Gable et al., "Mutations in the yeast *LCB1* and *LCB2* genes, including those corresponding to the hereditary sensory neuropathy type I mutations, dominantly Inactivate serine palmitoyltransferase," *Journal of Biological Chemistry* 277(12):10194-10200, Mar. 22, 2002.
Galvão et al., "Prolonged administration of FTY720 does not cause renal toxicity in mice," *Transplantation Proceedings* 37:112-113, 2005.
Gräler and Goetzl, "The immunosuppressant FTY720 down-regulates sphingosine 1-phosphate G-protein-coupled receptors," *FASEB Journal* 18:551-553, Mar. 2004.
Green and Reed, "Mitochondria and Apoptosis," *Science* 281:1309-1312, Aug. 28, 1998.
Harborth et al., "Identification of essential genes in cultured mammalian cells using small interfering RNAs," *Journal of Cell Science* 114(24):4557-4565, 2001.
Halin et al., "The S1P-analog FTY720 differentially modulates T-cell homing via HEV: T-cell-expressed $S1P_1$ amplifies integrin activation in peripheral lymph nodes not in Peyer patches," *Blood* 106(4):1314-1322, Aug. 15, 2005.
Herr et al., "*Sply* regulation of sphingolipid signaling molecules is essential for *Drosophila* development," *Development* 130:2443-2453, 2003.
Herskowitz, "Functional inactivation of genes by dominant negative mutations," *Nature* 329:219-222, Sep. 17, 1987.
Honig et al., "FTY720 stimulates multidrug transporter- and cysteinyl leukotriene-dependent T cell chemotaxis to lymph nodes," *Journal of Clinical Investigation* 111(5):627-637, Mar. 2003.
Hutvágner and Zamore, "RNAi: nature abhors a double-strand," *Current Opinion in Genetics & Development* 12:225-232, 2002.
Jäger et al., "Oligonucleotide *N*-Alkylphosphoramidates: Synthesis and binding to polynucleotides," *Biochemistry* 27:7237-7246, 1988.
Karagiannis and El-Osta, "RNA interference and potential therapeutic applications of short interfering RNAs," *Cancer Gene Therapy* 12:787-795, 2005.
Kataoka et al., "Immunosuppressive activity of FTY720, sphingosine 1-phosphate receptor agonist: II. Effect of FTY720 and FTY720-phosphate on host-versus-graft and graft-versus host reaction in mice," *Transplantation Proceedings* 37:107-109, 2005.
Kimura et al., "The sphingosine 1-phosphate receptor agonist FTY720 supports CXCR4-dependent migration and bone marrow homing of human CD34+ progenitor cells," *Blood* 103:4478-4486, Jun. 2004.
Kluck et al., "The release of cytochrome c from Mitochondria: A primary site for Bcl-2 regulation of apoptosis," *Science* 275:1132-1136, Feb. 21, 1997.
Letsinger et al., "Some developments in the phosphite-triester method for synthesis of oligonucleotides," *Tetrahedron* 40(1):137-143, 1984.
Li et al., "Sphingosine-1-phosphate lyase has a central role in the development of *Dictyostelium discoideum*," *Development* 128:3473-3483, 2001.
Liu et al., "Induction of apoptotic program in cell-free extracts: Requirement for dATP and Cytochrome c," *Cell* 86:147-157, Jul. 12, 1996.
Mandala et al., Alteration of lymphocyte trafficking by sphingosine-1-phosphate receptor agonists, *Science* 296:346-349, Apr. 12, 2002.

Matloubian et al., "Lymphocyte egress from thymus and peripheral lymphoid organs is dependent on S1P receptor 1," *Nature* 427:355-360, Jan. 22, 2004.

Matzke et al., "RNA: Guiding gene silencing," *Science* 293:1080-1083, Aug. 10, 2001.

Mendel et al., "Sphingosine phosphate lyase expression is essential for normal development in *Caenorhabditis elegans*," *Journal of Biological Chemistry* 278(25):22341-22349, Jun. 20, 2003.

Miller et al., "Syntheses and properties of adenine and thymine nucleoside alkyl phosphotriesters, the neutral analogs of dinucleoside monophosphates," *Journal of the American Chemical Society* 93(24):6657-6665, Dec. 1, 1971.

Mishell et al., "Preparation of mouse cell suspensions" in Mishell and Shiigi (eds.), *Selected Methods of Cellular Immunology*, W. H. Freeman and Company, San Francisco, California, 1980, pp. 3-27.

Moody et al., "Regiospecific inhibition of DNA duplication by antisense phosphate-methylated oligodeoxynucleotides," *Nucleic Acids Research* 17(12):4769-4782, 1989.

Nicholson et al., "Identification and inhibition of the ICE/CED-3 protease necessary for mammalian apoptosis," *Nature* 376:37-43, Jul. 6, 1995.

Nykänen et al., "ATP requirements and small interfering RNA structure in the RNA interference pathway," *Cell* 107:309-321, Nov. 2, 2001.

Ott and Cambier, "Activating and inhibitory signaling in mast cells: New opportunities for therapeutic intervention?" *Journal of Allergy and Clinical Immunology* 106(3):429-440, Sep. 2000.

Perlmutter and Alberola-Ila, "The use of dominant-negative mutations to elucidate signal transduction pathways in lymphocytes," *Current Opinion in Immunology* 8:285-290, 1996.

Pinschewer et al., "FTY720 immunosuppression impairs effector T cell peripheral homing without affecting induction, expansion, and memory," *Journal of Immunology* 164:5761-5770, 2000.

Plasterk, "RNA silencing: The genome's immune system," *Science* 296:1263-1265, May 17, 2002.

Rabinovitch, "DNA content histogram and cell-cycle analysis," in Darzynkiewicz et al. (eds.), *Methods in Cell Biology: Flow Cytometry 41*, 2d ed., Academic Press, San Diego, California, Nov. 7, 1994, pp. 263-296.

Rosen and Casciola-Rosen, "Macromolecular substrates for the ICE-like proteases during apoptosis," *Journal of Cellular Biochemistry* 64:50-54, 1997.

Saba, "Lysophospholipids in development: Miles apart and edging in," *Journal of Cellular Biochemistry* 92:967-992, 2004.

Saba and Hla, "Point-counterpoint of sphingosine 1-phosphate metabolism," *Circulation Research* 94:724-734, Apr. 12, 2004.

Sanchez et al., " Phosphorylation and action of the immunomodulator FTY720 inhibits vascular endothelial cell growth factor-induced vascular permeability," *Journal of Biological Chemistry* 278(47):47281-47290, Nov. 21, 2003.

Scadden and Smith, "RNAi is antagonized by A→I hyper-editing," *EMBO Reports* 2(12):1107-1111, 2001.

Schmid et al., FTY720 inhibits tumor growth and angiogenesis, *Transplantation Proceedings* 37:110-111, 2005.

Scountzou et al., "Inhibitory effect of deoxypyridoxine on the action of certain mitogenic factors," *Immunopharmacology and Immunotoxicology* 11(4):657-666, 1989.

Sharp, "RNAi and double-strand RNA," *Genes & Development* 13:139-141, 1999.

Sharp, "RNA interference—2001," *Genes & Development* 15:485-490, 2001.

Stec et al., "Synthesis and absolute configuration of P-chiral O-isopropyl oligonucleotide triesters," *Tetrahedron Letters* $\overline{26}$(18):2191-2194, 1985.

Stein and Cohen, *Oligodeoxynucleotides: Antisense Inhibitors of Gene Expression*, CRC Press, Inc., Boca Raton, Florida, 1989, Chapter 5, "Phosphorothioate oligodeoxynucleotide analogues," pp. 97-117.

Tedesco-Silva et al., "FTY720, a novel immunomodulator: Efficacy and safety results from the first phase 2A study in de novo renal transplantation," *Transplantation* 77(12):1826-1833, Jun. 27, 2004.

Togias, "Unique mechanistic features of allergic rhinitis," *Journal of Allergy and Clinical Immunology* 105(6 part 2):S599-5604, Jun. 2000.

Triola et al., "Specificity of the dihydroceramide desaturase inhibitor $N$-[(1$R$,2$S$)-2-hydroxy-1-hydroxymethyl-2-(2-tridecy1-1-cyclopropenypethyl]octanamide (GT11) in primary cultured cerebellar neurons," *Molecular Pharmacology* 66(6):1671-1678, 2004.

Thornberry and Lazebnik, "Caspases: Enemies within," *Science* 281:1312-1316, Aug. 28, 1998.

Tomari and Zamore, "Perspective: Machines for RNAi," *Genes & Development* 19:517-529, 2005.

Tuschl, "RNA interference and small interfering RNAs," *Chembiochem* 2:239-245, 2001.

Uznanski et al., "The isopropoxyacetic group for convenient base protection during solid-support synthesis of oligodeoxyribonucleotides and their triester analogs," *Nucleic Acids Research* 17(12):4863-4871, 1989.

Van Veldhoven and Mannaerts, "Subcellular localization and membrane topology of sphingosine-1-phosphate lyase in rat liver," *Journal of Biological Chemistry* 266(19):12502-12507, Jul. 5, 1991.

Vora et al., "Sphingosine 1-phosphate receptor agonist FTY720-phosphate causes marginal zone B cell displacement," *Journal of Leukocyte Biology* 78:471-480, Aug. 2005.

Wyllie, "Glucocorticoid-induced thymocyte apoptosis is associated with endogenous endonuclease activation," *Nature* 284:555-556, Apr. 10, 1980.

Xie et al., "Sphingosine-1-phosphate receptor agonism impairs the efficiency of the local immune response by altering trafficking of naive and antigen-activated CD4[+] T cells," *Journal of Immunology* 170:3662-3670, 2003.

Yan et al., "Control of intestinal allograft rejection by FTY720 and costimulation blockade," *Transplantation Proceedings* 37:114-115, 2005.

Zamore et al., "RNAi: Double-stranded RNA directs the ATP-dependent cleavage of mRNA at 21 to 23 nucleotide intervals," *Cell* 101:25-33, Mar. 31, 2000.

Zamore, "RNA interference: listening to the sound of silence," *Nature Structural Biology* 8(9):746-750, Sep. 2001.

Zamore, "Ancient pathways programmed by small RNAs," *Science* 296:1265-1269, May 17, 2002.

\* cited by examiner

SEQUENCE LISTING

```
<160> NUMBER OF SEQ ID NOS: 11

<210> SEQ ID NO 1
<211> LENGTH: 1707
<212> TYPE: DNA
<213> ORGANISM: Homo sapiens
<220> FEATURE:
<221> NAME/KEY: CDS
<222> LOCATION: (1)...(1707)

<400> SEQUENCE: 1 atg cct agc aca gac ctt ctg atg ttg aag gcc ttt gag ccc tac tta    48
Met Pro Ser Thr Asp Leu Leu Met Leu Lys Ala Phe Glu Pro Tyr Leu
1               5                   10                  15
```

```
gag att ttg gaa gta tac tcc aca aaa gcc aag aat tat gta aat gga        96
Glu Ile Leu Glu Val Tyr Ser Thr Lys Ala Lys Asn Tyr Val Asn Gly
            20                  25                  30 cat tgc acc aag tat gag ccc tgg cag cta att gca tgg agt gtc gtg       144
His Cys Thr Lys Tyr Glu Pro Trp Gln Leu Ile Ala Trp Ser Val Val
                35                  40                  45 tgg acc ctg ctg ata gtc tgg gga tat gag ttt gtc ttc cag cca gag       192
Trp Thr Leu Leu Ile Val Trp Gly Tyr Glu Phe Val Phe Gln Pro Glu
 50                  55                  60 agt tta tgg tca agg ttt aaa aag aaa tgt ttt aag ctc acc agg aag       240
Ser Leu Trp Ser Arg Phe Lys Lys Lys Cys Phe Lys Leu Thr Arg Lys
 65                  70                  75                  80 atg ccc att att ggt cgt aag att caa gac aag ttg aac aag acc aag       288
Met Pro Ile Ile Gly Arg Lys Ile Gln Asp Lys Leu Asn Lys Thr Lys
                 85                  90                  95 gat gat att agc aag aac atg tca ttc ctg aaa gtg gac aaa gag tat       336
Asp Asp Ile Ser Lys Asn Met Ser Phe Leu Lys Val Asp Lys Glu Tyr
                100                 105                 110 gtg aaa gct tta ccc tcc cag ggt ctg agc tca tct gct gtt ttg gag       384
Val Lys Ala Leu Pro Ser Gln Gly Leu Ser Ser Ser Ala Val Leu Glu
            115                 120                 125 aaa ctt aag gag tac agc tct atg gac gcc ttc tgg caa gag ggg aga       432
Lys Leu Lys Glu Tyr Ser Ser Met Asp Ala Phe Trp Gln Glu Gly Arg
130                 135                 140 gcc tct gga aca gtg tac agt ggg gag gag aag ctc act gag ctc ctt       480
Ala Ser Gly Thr Val Tyr Ser Gly Glu Glu Lys Leu Thr Glu Leu Leu
145                 150                 155                 160 gtg aag gct tat gga gat ttt gca tgg agt aac ccc ctg cat cca gat       528
Val Lys Ala Tyr Gly Asp Phe Ala Trp Ser Asn Pro Leu His Pro Asp
                165                 170                 175 atc ttc cca gga cta cgc aag ata gag gca gaa att gtg agg ata gct       576
Ile Phe Pro Gly Leu Arg Lys Ile Glu Ala Glu Ile Val Arg Ile Ala
                180                 185                 190 tgt tcc ctg ttc aat ggg gga cca gat tcg tgt gga tgt gtg act tct       624
Cys Ser Leu Phe Asn Gly Gly Pro Asp Ser Cys Gly Cys Val Thr Ser
            195                 200                 205 ggg gga aca gaa agc ata ctc atg gcc tgc aaa gca tgt cgg gat ctg       672
Gly Gly Thr Glu Ser Ile Leu Met Ala Cys Lys Ala Cys Arg Asp Leu
210                 215                 220 gcc ttt gag aag ggg atc aaa act cca gaa att gtg gct ccc caa agt       720
Ala Phe Glu Lys Gly Ile Lys Thr Pro Glu Ile Val Ala Pro Gln Ser
225                 230                 235                 240 gcc cat gct gca ttt aac aaa gca gcc agt tac ttt ggg atg aag att       768
Ala His Ala Ala Phe Asn Lys Ala Ala Ser Tyr Phe Gly Met Lys Ile
                245                 250                 255 gtg cgg gtc cca ttg acg aag atg atg gag gtg gat gtg agg gca atg       816
Val Arg Val Pro Leu Thr Lys Met Met Glu Val Asp Val Arg Ala Met
                260                 265                 270 aga aga gct atc tcc agg aac act gcc atg ctc gtc tgt tct acc cca       864
Arg Arg Ala Ile Ser Arg Asn Thr Ala Met Leu Val Cys Ser Thr Pro
            275                 280                 285 cag ttt cct cat ggt gta ata gat cct gtc cct gaa gtg gcc aag ctg       912
Gln Phe Pro His Gly Val Ile Asp Pro Val Pro Glu Val Ala Lys Leu
290                 295                 300 gct gtc aaa tac aaa ata ccc ctt cat gtc gac gct tgt ctg gga ggc       960
Ala Val Lys Tyr Lys Ile Pro Leu His Val Asp Ala Cys Leu Gly Gly
305                 310                 315                 320 ttc ctc atc gtc ttt atg gag aaa gca gga tac cca ctg gag cac cca      1008
Phe Leu Ile Val Phe Met Glu Lys Ala Gly Tyr Pro Leu Glu His Pro
                325                 330                 335
```

-continued

```
ttt gat ttc cgg gtg aaa ggt gta acc agc att tca gct gac acc cat    1056
Phe Asp Phe Arg Val Lys Gly Val Thr Ser Ile Ser Ala Asp Thr His
            340                 345                 350 aag tat ggc tat gcc cca aaa ggc tca tca ttg gtg ttg tat agt gac    1104
Lys Tyr Gly Tyr Ala Pro Lys Gly Ser Ser Leu Val Leu Tyr Ser Asp
        355                 360                 365 aag aag tac agg aac tat cag ttc ttc gtc gat aca gat tgg cag ggt    1152
Lys Lys Tyr Arg Asn Tyr Gln Phe Phe Val Asp Thr Asp Trp Gln Gly
    370                 375                 380 ggc atc tat gct tcc cca acc atc gca ggc tca cgg cct ggt ggc att    1200
Gly Ile Tyr Ala Ser Pro Thr Ile Ala Gly Ser Arg Pro Gly Gly Ile
385                 390                 395                 400 agc gca gcc tgt tgg gct gcc ttg atg cac ttc ggt gag aac ggc tat    1248
Ser Ala Ala Cys Trp Ala Ala Leu Met His Phe Gly Glu Asn Gly Tyr
                405                 410                 415 gtt gaa gct acc aaa cag atc atc aaa act gct cgc ttc ctc aag tca    1296
Val Glu Ala Thr Lys Gln Ile Ile Lys Thr Ala Arg Phe Leu Lys Ser
            420                 425                 430 gaa ctg gaa aat atc aaa ggc atc ttt gtt ttt ggg aat ccc caa ttg    1344
Glu Leu Glu Asn Ile Lys Gly Ile Phe Val Phe Gly Asn Pro Gln Leu
        435                 440                 445 tca ctc att gct ctg gga tcc cgt gat ttt gac atc tac cga cta tca    1392
Ser Leu Ile Ala Leu Gly Ser Arg Asp Phe Asp Ile Tyr Arg Leu Ser
    450                 455                 460 aac ctg atg act gct aag ggg tgg aac ttg aac cag ttg cag ttc cca    1440
Asn Leu Met Thr Ala Lys Gly Trp Asn Leu Asn Gln Leu Gln Phe Pro
465                 470                 475                 480 ccc agt att cat ttc tgc atc aca tta cta cac gcc cgg aaa cga gta    1488
Pro Ser Ile His Phe Cys Ile Thr Leu Leu His Ala Arg Lys Arg Val
                485                 490                 495 gct ata caa ttc cta aag gac att cga gaa tct gtc act caa atc atg    1536
Ala Ile Gln Phe Leu Lys Asp Ile Arg Glu Ser Val Thr Gln Ile Met
            500                 505                 510 aag aat cct aaa gcg aag acc aca gga atg ggt gcc atc tat gcc atg    1584
Lys Asn Pro Lys Ala Lys Thr Thr Gly Met Gly Ala Ile Tyr Ala Met
        515                 520                 525 gcc cag aca act gtt gac agg aat atg gtt gca gaa ttg tcc tca gtc    1632
Ala Gln Thr Thr Val Asp Arg Asn Met Val Ala Glu Leu Ser Ser Val
    530                 535                 540 ttc ttg gac agc ttg tac agc acc gac act gtc acc cag ggc agc cag    1680
Phe Leu Asp Ser Leu Tyr Ser Thr Asp Thr Val Thr Gln Gly Ser Gln
545                 550                 555                 560 atg aat ggt tct cca aaa ccc cac tga                                1707
Met Asn Gly Ser Pro Lys Pro His *
                565

<210> SEQ ID NO 2
<211> LENGTH: 568
<212> TYPE: PRT
<213> ORGANISM: Homo sapiens

<400> SEQUENCE: 2

Met Pro Ser Thr Asp Leu Leu Met Leu Lys Ala Phe Glu Pro Tyr Leu
 1               5                  10                  15

Glu Ile Leu Glu Val Tyr Ser Thr Lys Ala Lys Asn Tyr Val Asn Gly
            20                  25                  30

His Cys Thr Lys Tyr Glu Pro Trp Gln Leu Ile Ala Trp Ser Val Val
        35                  40                  45

Trp Thr Leu Leu Ile Val Trp Gly Tyr Glu Phe Val Phe Gln Pro Glu
    50                  55                  60
```

```
Ser Leu Trp Ser Arg Phe Lys Lys Cys Phe Lys Leu Thr Arg Lys
 65                  70                  75                  80

Met Pro Ile Ile Gly Arg Lys Ile Gln Asp Lys Leu Asn Lys Thr Lys
                     85                  90                  95

Asp Asp Ile Ser Lys Asn Met Ser Phe Leu Lys Val Asp Lys Glu Tyr
                100                 105                 110

Val Lys Ala Leu Pro Ser Gln Gly Leu Ser Ser Ala Val Leu Glu
            115                 120                 125

Lys Leu Lys Glu Tyr Ser Ser Met Asp Ala Phe Trp Gln Glu Gly Arg
130                 135                 140

Ala Ser Gly Thr Val Tyr Ser Gly Glu Glu Lys Leu Thr Glu Leu Leu
145                 150                 155                 160

Val Lys Ala Tyr Gly Asp Phe Ala Trp Ser Asn Pro Leu His Pro Asp
                165                 170                 175

Ile Phe Pro Gly Leu Arg Lys Ile Glu Ala Glu Ile Val Arg Ile Ala
                180                 185                 190

Cys Ser Leu Phe Asn Gly Gly Pro Asp Ser Cys Gly Cys Val Thr Ser
            195                 200                 205

Gly Gly Thr Glu Ser Ile Leu Met Ala Cys Lys Ala Cys Arg Asp Leu
            210                 215                 220

Ala Phe Glu Lys Gly Ile Lys Thr Pro Glu Ile Val Ala Pro Gln Ser
225                 230                 235                 240

Ala His Ala Ala Phe Asn Lys Ala Ala Ser Tyr Phe Gly Met Lys Ile
                245                 250                 255

Val Arg Val Pro Leu Thr Lys Met Met Glu Val Asp Val Arg Ala Met
                260                 265                 270

Arg Arg Ala Ile Ser Arg Asn Thr Ala Met Leu Val Cys Ser Thr Pro
            275                 280                 285

Gln Phe Pro His Gly Val Ile Asp Pro Val Pro Glu Val Ala Lys Leu
            290                 295                 300

Ala Val Lys Tyr Lys Ile Pro Leu His Val Asp Ala Cys Leu Gly Gly
305                 310                 315                 320

Phe Leu Ile Val Phe Met Glu Lys Ala Gly Tyr Pro Leu Glu His Pro
                325                 330                 335

Phe Asp Phe Arg Val Lys Gly Val Thr Ser Ile Ser Ala Asp Thr His
                340                 345                 350

Lys Tyr Gly Tyr Ala Pro Lys Gly Ser Ser Leu Val Leu Tyr Ser Asp
            355                 360                 365

Lys Lys Tyr Arg Asn Tyr Gln Phe Phe Val Asp Thr Asp Trp Gln Gly
370                 375                 380

Gly Ile Tyr Ala Ser Pro Thr Ile Ala Gly Ser Arg Pro Gly Gly Ile
385                 390                 395                 400

Ser Ala Ala Cys Trp Ala Ala Leu Met His Phe Gly Glu Asn Gly Tyr
                405                 410                 415

Val Glu Ala Thr Lys Gln Ile Ile Lys Thr Ala Arg Phe Leu Lys Ser
                420                 425                 430

Glu Leu Glu Asn Ile Lys Gly Ile Phe Val Phe Gly Asn Pro Gln Leu
            435                 440                 445

Ser Leu Ile Ala Leu Gly Ser Arg Asp Phe Asp Ile Tyr Arg Leu Ser
            450                 455                 460

Asn Leu Met Thr Ala Lys Gly Trp Asn Leu Asn Gln Leu Gln Phe Pro
465                 470                 475                 480

Pro Ser Ile His Phe Cys Ile Thr Leu Leu His Ala Arg Lys Arg Val
```

```
                           485                 490                 495
Ala Ile Gln Phe Leu Lys Asp Ile Arg Glu Ser Val Thr Gln Ile Met
            500                 505                 510

Lys Asn Pro Lys Ala Lys Thr Thr Gly Met Gly Ala Ile Tyr Ala Met
            515                 520                 525

Ala Gln Thr Thr Val Asp Arg Asn Met Val Ala Glu Leu Ser Ser Val
            530                 535                 540

Phe Leu Asp Ser Leu Tyr Ser Thr Asp Thr Val Thr Gln Gly Ser Gln
545                 550                 555                 560

Met Asn Gly Ser Pro Lys Pro His
            565

<210> SEQ ID NO 3
<211> LENGTH: 1707
<212> TYPE: DNA
<213> ORGANISM: Mus musculus
<220> FEATURE:
<221> NAME/KEY: CDS
<222> LOCATION: (1)...(1707)

<400> SEQUENCE: 3 atg ccc gga acc gac ctc ctc aag ctg aag gac ttc gag cct tat ttg      48
Met Pro Gly Thr Asp Leu Leu Lys Leu Lys Asp Phe Glu Pro Tyr Leu
1               5                   10                  15 gag att ttg gaa tct tat tcc aca aaa gcc aag aat tat gtg aat gga      96
Glu Ile Leu Glu Ser Tyr Ser Thr Lys Ala Lys Asn Tyr Val Asn Gly
                20                  25                  30 tat tgc acc aaa tat gag ccc tgg cag ctc att gcg tgg agt gtc ctg     144
Tyr Cys Thr Lys Tyr Glu Pro Trp Gln Leu Ile Ala Trp Ser Val Leu
            35                  40                  45 tgt act ctg ctg ata gtc tgg gtg tat gag ctt atc ttc cag cca gag     192
Cys Thr Leu Leu Ile Val Trp Val Tyr Glu Leu Ile Phe Gln Pro Glu
        50                  55                  60 agt tta tgg tct cgg ttt aaa aaa aaa tta ttt aag ctt atc agg aag     240
Ser Leu Trp Ser Arg Phe Lys Lys Lys Leu Phe Lys Leu Ile Arg Lys
65                  70                  75                  80 atg cca ttt att gga cgt aag atc gaa caa cag gtg agc aaa gcc aag     288
Met Pro Phe Ile Gly Arg Lys Ile Glu Gln Gln Val Ser Lys Ala Lys
                85                  90                  95 aag gat ctt gtc aag aac atg cca ttc cta aag gtg gac aag gat tat     336
Lys Asp Leu Val Lys Asn Met Pro Phe Leu Lys Val Asp Lys Asp Tyr
            100                 105                 110 gtg aaa act ctg cct gct cag ggt atg ggc aca gct gag gtt ctg gag     384
Val Lys Thr Leu Pro Ala Gln Gly Met Gly Thr Ala Glu Val Leu Glu
        115                 120                 125 aga ctc aag gag tac agc tcc atg gat ggt tcc tgg caa gaa ggg aaa     432
Arg Leu Lys Glu Tyr Ser Ser Met Asp Gly Ser Trp Gln Glu Gly Lys
    130                 135                 140 gcc tca gga gct gtg tac aat ggg gaa ccg aag ctc acg gag ctg ctg     480
Ala Ser Gly Ala Val Tyr Asn Gly Glu Pro Lys Leu Thr Glu Leu Leu
145                 150                 155                 160 gtg cag gct tat gga gaa ttc acg tgg agc aat cca ctg cat cca gat     528
Val Gln Ala Tyr Gly Glu Phe Thr Trp Ser Asn Pro Leu His Pro Asp
                165                 170                 175 atc ttc cct gga ttg cgg aag tta gag gca gaa atc gtt agg atg act     576
Ile Phe Pro Gly Leu Arg Lys Leu Glu Ala Glu Ile Val Arg Met Thr
            180                 185                 190 tgt tcc ctc ttc aat ggg gga cca gat tcc tgt gga tgt gtg act tct     624
Cys Ser Leu Phe Asn Gly Gly Pro Asp Ser Cys Gly Cys Val Thr Ser
        195                 200                 205
```

| | | |
|---|---|---|
| ggg gga acg gaa agc atc ctg atg gcc tgc aaa gct tac cgg gac ttg<br>Gly Gly Thr Glu Ser Ile Leu Met Ala Cys Lys Ala Tyr Arg Asp Leu<br>210                           215                      220 | | 672 |
| gcg tta gag aag ggg atc aaa act cca gaa att gtg gct ccc gag agt<br>Ala Leu Glu Lys Gly Ile Lys Thr Pro Glu Ile Val Ala Pro Glu Ser<br>225                       230                       235                   240 | | 720 |
| gcc cat gct gca ttc gac aaa gca gct cat tat ttt ggg atg aag att<br>Ala His Ala Ala Phe Asp Lys Ala Ala His Tyr Phe Gly Met Lys Ile<br>                       245                       250                   255 | | 768 |
| gtc cga gtt gca ctg aaa aag aac atg gag gtg gat gtg cag gca atg<br>Val Arg Val Ala Leu Lys Lys Asn Met Glu Val Asp Val Gln Ala Met<br>             260                     265                     270 | | 816 |
| aag aga gcc atc tcc agg aac aca gct atg ctg gtc tgt tct acc cca<br>Lys Arg Ala Ile Ser Arg Asn Thr Ala Met Leu Val Cys Ser Thr Pro<br>275                       280                       285 | | 864 |
| cag ttt cct cat ggt gtg atg gat cct gtc ccc gaa gtg gcc aag tta<br>Gln Phe Pro His Gly Val Met Asp Pro Val Pro Glu Val Ala Lys Leu<br>       290                     295                     300 | | 912 |
| act gtc aga tat aaa atc cca ctc cat gtg gat gct tgt ctg ggg ggc<br>Thr Val Arg Tyr Lys Ile Pro Leu His Val Asp Ala Cys Leu Gly Gly<br>305                       310                       315                   320 | | 960 |
| ttc ctc att gtc ttc atg gag aaa gca ggg tac cca ctg gag aaa cca<br>Phe Leu Ile Val Phe Met Glu Lys Ala Gly Tyr Pro Leu Glu Lys Pro<br>                     325                       330                   335 | | 1008 |
| ttt gat ttc cgg gtg aaa ggt gtg acc agc att tca gca gat act cat<br>Phe Asp Phe Arg Val Lys Gly Val Thr Ser Ile Ser Ala Asp Thr His<br>             340                     345                     350 | | 1056 |
| aag tat ggc tat gct cct aaa ggt tca tca gtg gtg atg tac tct aac<br>Lys Tyr Gly Tyr Ala Pro Lys Gly Ser Ser Val Val Met Tyr Ser Asn<br>                   355                     360                   365 | | 1104 |
| gag aag tac agg acg tac cag ttc ttt gtt ggt gca gac tgg caa ggt<br>Glu Lys Tyr Arg Thr Tyr Gln Phe Phe Val Gly Ala Asp Trp Gln Gly<br>       370                     375                     380 | | 1152 |
| ggt gtc tac gca tct cca agc ata gct ggc tca cgg cct ggt ggc atc<br>Gly Val Tyr Ala Ser Pro Ser Ile Ala Gly Ser Arg Pro Gly Gly Ile<br>385                       390                       395                   400 | | 1200 |
| att gca gcc tgt tgg gcg gcc ttg atg cac ttc ggt gag aac ggc tat<br>Ile Ala Ala Cys Trp Ala Ala Leu Met His Phe Gly Glu Asn Gly Tyr<br>                     405                     410                   415 | | 1248 |
| gtt gaa gct acc aaa cag atc atc aaa act gct cgc ttc ctg aag tca<br>Val Glu Ala Thr Lys Gln Ile Ile Lys Thr Ala Arg Phe Leu Lys Ser<br>             420                     425                     430 | | 1296 |
| gaa ctg gaa aac atc aaa aac atc ttc att ttc ggt gat cct caa ttg<br>Glu Leu Glu Asn Ile Lys Asn Ile Phe Ile Phe Gly Asp Pro Gln Leu<br>                   435                     440                   445 | | 1344 |
| tca gtt att gct ctg gga tcc aac gat ttt gac att tac cga cta tct<br>Ser Val Ile Ala Leu Gly Ser Asn Asp Phe Asp Ile Tyr Arg Leu Ser<br>450                       455                       460 | | 1392 |
| aat atg atg tct gct aag ggg tgg aat ttt aac tac ctg cag ttc cca<br>Asn Met Met Ser Ala Lys Gly Trp Asn Phe Asn Tyr Leu Gln Phe Pro<br>465                       470                       475                   480 | | 1440 |
| aga agc att cat ttc tgc att acg tta gta cat act cgg aag cga gtg<br>Arg Ser Ile His Phe Cys Ile Thr Leu Val His Thr Arg Lys Arg Val<br>                   485                     490                     495 | | 1488 |
| gcg atc cag ttc cta aag gat atc cgg gaa tca gtc aca caa atc atg<br>Ala Ile Gln Phe Leu Lys Asp Ile Arg Glu Ser Val Thr Gln Ile Met<br>       500                     505                     510 | | 1536 |
| aag aat cct aaa gct aag acc aca gga atg ggt gcc atc tat ggc atg<br>Lys Asn Pro Lys Ala Lys Thr Thr Gly Met Gly Ala Ile Tyr Gly Met<br>515                       520                       525 | | 1584 |

```
gcc cag gca acc att gac agg aag ctg gtt gca gaa ata tcc tcc gtc    1632
Ala Gln Ala Thr Ile Asp Arg Lys Leu Val Ala Glu Ile Ser Ser Val
    530                 535                 540 ttc ttg gac tgc ctt tat act acg gac ccc gtg act cag ggc aac cag    1680
Phe Leu Asp Cys Leu Tyr Thr Thr Asp Pro Val Thr Gln Gly Asn Gln
545                 550                 555                 560 atg aac ggt tct cca aag ccc cgc tga                                1707
Met Asn Gly Ser Pro Lys Pro Arg *
                565

<210> SEQ ID NO 4
<211> LENGTH: 568
<212> TYPE: PRT
<213> ORGANISM: Mus musculus

<400> SEQUENCE: 4

Met Pro Gly Thr Asp Leu Leu Lys Leu Lys Asp Phe Glu Pro Tyr Leu
1               5                   10                  15

Glu Ile Leu Glu Ser Tyr Ser Thr Lys Ala Lys Asn Tyr Val Asn Gly
            20                  25                  30

Tyr Cys Thr Lys Tyr Glu Pro Trp Gln Leu Ile Ala Trp Ser Val Leu
        35                  40                  45

Cys Thr Leu Leu Ile Val Trp Val Tyr Glu Leu Ile Phe Gln Pro Glu
    50                  55                  60

Ser Leu Trp Ser Arg Phe Lys Lys Lys Leu Phe Lys Leu Ile Arg Lys
65                  70                  75                  80

Met Pro Phe Ile Gly Arg Lys Ile Glu Gln Gln Val Ser Lys Ala Lys
                85                  90                  95

Lys Asp Leu Val Lys Asn Met Pro Phe Leu Lys Val Asp Lys Asp Tyr
            100                 105                 110

Val Lys Thr Leu Pro Ala Gln Gly Met Gly Thr Ala Glu Val Leu Glu
        115                 120                 125

Arg Leu Lys Glu Tyr Ser Ser Met Asp Gly Ser Trp Gln Glu Gly Lys
    130                 135                 140

Ala Ser Gly Ala Val Tyr Asn Gly Glu Pro Lys Leu Thr Glu Leu Leu
145                 150                 155                 160

Val Gln Ala Tyr Gly Glu Phe Thr Trp Ser Asn Pro Leu His Pro Asp
                165                 170                 175

Ile Phe Pro Gly Leu Arg Lys Leu Glu Ala Glu Ile Val Arg Met Thr
            180                 185                 190

Cys Ser Leu Phe Asn Gly Gly Pro Asp Ser Cys Gly Cys Val Thr Ser
        195                 200                 205

Gly Gly Thr Glu Ser Ile Leu Met Ala Cys Lys Ala Tyr Arg Asp Leu
    210                 215                 220

Ala Leu Glu Lys Gly Ile Lys Thr Pro Glu Ile Val Ala Pro Glu Ser
225                 230                 235                 240

Ala His Ala Ala Phe Asp Lys Ala His Tyr Phe Gly Met Lys Ile
                245                 250                 255

Val Arg Val Ala Leu Lys Lys Asn Met Glu Val Asp Val Gln Ala Met
            260                 265                 270

Lys Arg Ala Ile Ser Arg Asn Thr Ala Met Leu Val Cys Ser Thr Pro
        275                 280                 285

Gln Phe Pro His Gly Val Met Asp Pro Val Pro Glu Val Ala Lys Leu
    290                 295                 300

Thr Val Arg Tyr Lys Ile Pro Leu His Val Asp Ala Cys Leu Gly Gly
305                 310                 315                 320
```

```
Phe Leu Ile Val Phe Met Glu Lys Ala Gly Tyr Pro Leu Glu Lys Pro
                325                 330                 335

Phe Asp Phe Arg Val Lys Gly Val Thr Ser Ile Ser Ala Asp Thr His
            340                 345                 350

Lys Tyr Gly Tyr Ala Pro Lys Gly Ser Ser Val Val Met Tyr Ser Asn
        355                 360                 365

Glu Lys Tyr Arg Thr Tyr Gln Phe Phe Val Gly Ala Asp Trp Gln Gly
    370                 375                 380

Gly Val Tyr Ala Ser Pro Ser Ile Ala Gly Ser Arg Pro Gly Gly Ile
385                 390                 395                 400

Ile Ala Ala Cys Trp Ala Ala Leu Met His Phe Gly Glu Asn Gly Tyr
                405                 410                 415

Val Glu Ala Thr Lys Gln Ile Ile Lys Thr Ala Arg Phe Leu Lys Ser
            420                 425                 430

Glu Leu Glu Asn Ile Lys Asn Ile Phe Ile Phe Gly Asp Pro Gln Leu
        435                 440                 445

Ser Val Ile Ala Leu Gly Ser Asn Asp Phe Asp Ile Tyr Arg Leu Ser
    450                 455                 460

Asn Met Met Ser Ala Lys Gly Trp Asn Phe Asn Tyr Leu Gln Phe Pro
465                 470                 475                 480

Arg Ser Ile His Phe Cys Ile Thr Leu Val His Thr Arg Lys Arg Val
                485                 490                 495

Ala Ile Gln Phe Leu Lys Asp Ile Arg Glu Ser Val Thr Gln Ile Met
            500                 505                 510

Lys Asn Pro Lys Ala Lys Thr Thr Gly Met Gly Ala Ile Tyr Gly Met
        515                 520                 525

Ala Gln Ala Thr Ile Asp Arg Lys Leu Val Ala Glu Ile Ser Ser Val
    530                 535                 540

Phe Leu Asp Cys Leu Tyr Thr Thr Asp Pro Val Thr Gln Gly Asn Gln
545                 550                 555                 560

Met Asn Gly Ser Pro Lys Pro Arg
                565

<210> SEQ ID NO 5
<211> LENGTH: 1467
<212> TYPE: DNA
<213> ORGANISM: Homo sapiens
<220> FEATURE:
<221> NAME/KEY: CDS
<222> LOCATION: (1)...(1467)

<400> SEQUENCE: 5 atg cct agc aca gac ctt ctg atg ttg aag gcc ttt gag ccc tac tta      48
Met Pro Ser Thr Asp Leu Leu Met Leu Lys Ala Phe Glu Pro Tyr Leu
1               5                   10                  15 gag att ttg gaa gta tac tcc aca aaa gcc aag aat tat gta aat gga      96
Glu Ile Leu Glu Val Tyr Ser Thr Lys Ala Lys Asn Tyr Val Asn Gly
            20                  25                  30 cat tgc acc aag tat gag ccc tgg cag cta att gca tgg agt gtc gtg     144
His Cys Thr Lys Tyr Glu Pro Trp Gln Leu Ile Ala Trp Ser Val Val
        35                  40                  45 tgg acc ctg ctg ata gtc tgg gga tat gag ttt gtc ttc cag cca gag     192
Trp Thr Leu Leu Ile Val Trp Gly Tyr Glu Phe Val Phe Gln Pro Glu
    50                  55                  60 agt tta tgg tca agg ttt aaa aag aaa tgt ttt aag ctc acc agg aag     240
Ser Leu Trp Ser Arg Phe Lys Lys Lys Cys Phe Lys Leu Thr Arg Lys
65                  70                  75                  80 atg ccc att att ggt cgt aag att caa gac aag ttg aac aag acc aag     288
```

|  |  |  |  |  |  |  |  |  |  |  |  |
|---|---|---|---|---|---|---|---|---|---|---|---|
| Met | Pro | Ile | Ile | Gly | Arg | Lys | Ile | Gln | Asp | Lys | Leu | Asn | Lys | Thr | Lys |
|  |  |  |  | 85 |  |  |  | 90 |  |  |  | 95 |  |  |  |

```
gat gat att agc aag aac atg tca ttc ctg aaa gtg gac aaa gag tat      336
Asp Asp Ile Ser Lys Asn Met Ser Phe Leu Lys Val Asp Lys Glu Tyr
            100                 105                 110 gtg aaa gct tta ccc tcc cag ggt ctg agc tca tct gct gtt ttg gag      384
Val Lys Ala Leu Pro Ser Gln Gly Leu Ser Ser Ser Ala Val Leu Glu
            115                 120                 125 aaa ctt aag gag tac agc tct atg gac gcc ttc tgg caa gag ggg aga      432
Lys Leu Lys Glu Tyr Ser Ser Met Asp Ala Phe Trp Gln Glu Gly Arg
130             135                 140 gcc tct gga aca gtg tac agt ggg gag gag aag ctc act gag ctc ctt      480
Ala Ser Gly Thr Val Tyr Ser Gly Glu Glu Lys Leu Thr Glu Leu Leu
145             150                 155                 160 gtg aag gct tat gga gat ttt gca tgg agt aac ccc ctg cat cca gat      528
Val Lys Ala Tyr Gly Asp Phe Ala Trp Ser Asn Pro Leu His Pro Asp
                165                 170                 175 atc ttc cca gga cta cgc aag ata gag gca gaa att gtg agg ata gct      576
Ile Phe Pro Gly Leu Arg Lys Ile Glu Ala Glu Ile Val Arg Ile Ala
            180                 185                 190 tgt tcc ctg ttc aat ggg gga cca gat tcg tgt gga tgt gtg act tct      624
Cys Ser Leu Phe Asn Gly Gly Pro Asp Ser Cys Gly Cys Val Thr Ser
            195                 200                 205 ggg gga aca gaa agc ata ctc atg gcc tgc aaa gca tgt cgg gat ctg      672
Gly Gly Thr Glu Ser Ile Leu Met Ala Cys Lys Ala Cys Arg Asp Leu
210             215                 220 gcc ttt gag aag ggg atc aaa act cca gaa att gtg gct ccc caa agt      720
Ala Phe Glu Lys Gly Ile Lys Thr Pro Glu Ile Val Ala Pro Gln Ser
225             230                 235                 240 gcc cat gct gca ttt aac aaa gca gcc agt tac ttt ggg atg aag att      768
Ala His Ala Ala Phe Asn Lys Ala Ala Ser Tyr Phe Gly Met Lys Ile
                245                 250                 255 gtg cgg gtc cca ttg acg aag atg atg gag gtg gat gtg agg gca atg      816
Val Arg Val Pro Leu Thr Lys Met Met Glu Val Asp Val Arg Ala Met
            260                 265                 270 aga aga gct atc tcc agg aac act gcc atg ctc gtc tgt tct acc cca      864
Arg Arg Ala Ile Ser Arg Asn Thr Ala Met Leu Val Cys Ser Thr Pro
            275                 280                 285 cag ttt cct cat ggt gta ata gat cct gtc cct gaa gtg gcc aag ctg      912
Gln Phe Pro His Gly Val Ile Asp Pro Val Pro Glu Val Ala Lys Leu
290             295                 300 gct gtc aaa tac aaa ata ccc ctt cat gtc gac gct tgt ctg gga ggc      960
Ala Val Lys Tyr Lys Ile Pro Leu His Val Asp Ala Cys Leu Gly Gly
305             310                 315                 320 ttc ctc atc gtc ttt atg gag aaa gca gga tac cca ctg gag cac cca     1008
Phe Leu Ile Val Phe Met Glu Lys Ala Gly Tyr Pro Leu Glu His Pro
                325                 330                 335 ttt gat ttc cgg gtg aaa ggt gta acc agc att tca gct gac acc cat     1056
Phe Asp Phe Arg Val Lys Gly Val Thr Ser Ile Ser Ala Asp Thr His
            340                 345                 350 aag ctg gaa aat atc aaa ggc atc ttt gtt ttt ggg aat ccc caa ttg     1104
Lys Leu Glu Asn Ile Lys Gly Ile Phe Val Phe Gly Asn Pro Gln Leu
            355                 360                 365 tca ctc att gct ctg gga tcc cgt gat ttt gac atc tac cga cta tca     1152
Ser Leu Ile Ala Leu Gly Ser Arg Asp Phe Asp Ile Tyr Arg Leu Ser
370             375                 380 aac ctg atg act gct aag ggg tgg aac ttg aac cag ttg cag ttc cca     1200
Asn Leu Met Thr Ala Lys Gly Trp Asn Leu Asn Gln Leu Gln Phe Pro
385             390                 395                 400 ccc agt att cat ttc tgc atc aca tta cta cac gcc cgg aaa cga gta     1248
```

```
                Pro Ser Ile His Phe Cys Ile Thr Leu Leu His Ala Arg Lys Arg Val
                                405                 410                 415 gct ata caa ttc cta aag gac att cga gaa tct gtc act caa atc atg           1296
Ala Ile Gln Phe Leu Lys Asp Ile Arg Glu Ser Val Thr Gln Ile Met
            420                 425                 430 aag aat cct aaa gcg aag acc aca gga atg ggt gcc atc tat gcc atg           1344
Lys Asn Pro Lys Ala Lys Thr Thr Gly Met Gly Ala Ile Tyr Ala Met
        435                 440                 445 gcc cag aca act gtt gac agg aat atg gtt gca gaa ttg tcc tca gtc           1392
Ala Gln Thr Thr Val Asp Arg Asn Met Val Ala Glu Leu Ser Ser Val
    450                 455                 460 ttc ttg gac agc ttg tac agc acc gac act gtc acc cag ggc agc cag           1440
Phe Leu Asp Ser Leu Tyr Ser Thr Asp Thr Val Thr Gln Gly Ser Gln
465                 470                 475                 480 atg aat ggt tct cca aaa ccc cac tga                                       1467
Met Asn Gly Ser Pro Lys Pro His  *
                485

<210> SEQ ID NO 6
<211> LENGTH: 488
<212> TYPE: PRT
<213> ORGANISM: Homo sapiens

<400> SEQUENCE: 6

Met Pro Ser Thr Asp Leu Leu Met Leu Lys Ala Phe Glu Pro Tyr Leu
 1               5                  10                  15

Glu Ile Leu Glu Val Tyr Ser Thr Lys Ala Lys Asn Tyr Val Asn Gly
            20                  25                  30

His Cys Thr Lys Tyr Glu Pro Trp Gln Leu Ile Ala Trp Ser Val Val
        35                  40                  45

Trp Thr Leu Leu Ile Val Trp Gly Tyr Glu Phe Val Phe Gln Pro Glu
    50                  55                  60

Ser Leu Trp Ser Arg Phe Lys Lys Cys Phe Lys Leu Thr Arg Lys
65                  70                  75                  80

Met Pro Ile Ile Gly Arg Lys Ile Gln Asp Lys Leu Asn Lys Thr Lys
                85                  90                  95

Asp Asp Ile Ser Lys Asn Met Ser Phe Leu Lys Val Asp Lys Glu Tyr
            100                 105                 110

Val Lys Ala Leu Pro Ser Gln Gly Leu Ser Ser Ala Val Leu Glu
        115                 120                 125

Lys Leu Lys Glu Tyr Ser Ser Met Asp Ala Phe Trp Gln Glu Gly Arg
    130                 135                 140

Ala Ser Gly Thr Val Tyr Ser Gly Glu Glu Lys Leu Thr Glu Leu Leu
145                 150                 155                 160

Val Lys Ala Tyr Gly Asp Phe Ala Trp Ser Asn Pro Leu His Pro Asp
                165                 170                 175

Ile Phe Pro Gly Leu Arg Lys Ile Glu Ala Glu Ile Val Arg Ile Ala
            180                 185                 190

Cys Ser Leu Phe Asn Gly Gly Pro Asp Ser Cys Gly Cys Val Thr Ser
        195                 200                 205

Gly Gly Thr Glu Ser Ile Leu Met Ala Cys Lys Ala Cys Arg Asp Leu
    210                 215                 220

Ala Phe Glu Lys Gly Ile Lys Thr Pro Glu Ile Val Ala Pro Gln Ser
225                 230                 235                 240

Ala His Ala Ala Phe Asn Lys Ala Ala Ser Tyr Phe Gly Met Lys Ile
                245                 250                 255

Val Arg Val Pro Leu Thr Lys Met Met Glu Val Asp Val Arg Ala Met
```

```
                  260                265                270
Arg Arg Ala Ile Ser Arg Asn Thr Ala Met Leu Val Cys Ser Thr Pro
        275                280                285

Gln Phe Pro His Gly Val Ile Asp Pro Val Pro Glu Val Ala Lys Leu
        290                295                300

Ala Val Lys Tyr Lys Ile Pro Leu His Val Asp Ala Cys Leu Gly Gly
305                310                315                320

Phe Leu Ile Val Phe Met Glu Lys Ala Gly Tyr Pro Leu Glu His Pro
                325                330                335

Phe Asp Phe Arg Val Lys Gly Val Thr Ser Ile Ser Ala Asp Thr His
                340                345                350

Lys Leu Glu Asn Ile Lys Gly Ile Phe Val Phe Gly Asn Pro Gln Leu
        355                360                365

Ser Leu Ile Ala Leu Gly Ser Arg Asp Phe Asp Ile Tyr Arg Leu Ser
        370                375                380

Asn Leu Met Thr Ala Lys Gly Trp Asn Leu Asn Gln Leu Gln Phe Pro
385                390                395                400

Pro Ser Ile His Phe Cys Ile Thr Leu Leu His Ala Arg Lys Arg Val
                405                410                415

Ala Ile Gln Phe Leu Lys Asp Ile Arg Glu Ser Val Thr Gln Ile Met
                420                425                430

Lys Asn Pro Lys Ala Lys Thr Thr Gly Met Gly Ala Ile Tyr Ala Met
                435                440                445

Ala Gln Thr Thr Val Asp Arg Asn Met Val Ala Glu Leu Ser Ser Val
450                455                460

Phe Leu Asp Ser Leu Tyr Ser Thr Asp Thr Val Thr Gln Gly Ser Gln
465                470                475                480

Met Asn Gly Ser Pro Lys Pro His
                485

<210> SEQ ID NO 7
<211> LENGTH: 1707
<212> TYPE: DNA
<213> ORGANISM: Homo sapiens
<220> FEATURE:
<221> NAME/KEY: CDS
<222> LOCATION: (1)...(1707)

<400> SEQUENCE: 7 atg cct agc aca gac ctt ctg atg ttg aag gcc ttt gag ccc tac tta      48
Met Pro Ser Thr Asp Leu Leu Met Leu Lys Ala Phe Glu Pro Tyr Leu
1               5                   10                  15 gag att ttg gaa gta tac tcc aca aaa gcc aag aat tat gta aat gga      96
Glu Ile Leu Glu Val Tyr Ser Thr Lys Ala Lys Asn Tyr Val Asn Gly
            20                  25                  30 cat tgc acc aag tat gag ccc tgg cag cta att gca tgg agt gtc gtg     144
His Cys Thr Lys Tyr Glu Pro Trp Gln Leu Ile Ala Trp Ser Val Val
        35                  40                  45 tgg acc ctg ctg ata gtc tgg gga tat gag ttt gtc ttc cag cca gag     192
Trp Thr Leu Leu Ile Val Trp Gly Tyr Glu Phe Val Phe Gln Pro Glu
    50                  55                  60 agt tta tgg tca agg ttt aaa aag aaa tgt ttt aag ctc acc agg aag     240
Ser Leu Trp Ser Arg Phe Lys Lys Lys Cys Phe Lys Leu Thr Arg Lys
65                  70                  75                  80 atg ccc att att ggt cgt aag att caa gac aag ttg aac aag acc aag     288
Met Pro Ile Ile Gly Arg Lys Ile Gln Asp Lys Leu Asn Lys Thr Lys
                85                  90                  95 gat gat att agc aag aac atg tca ttc ctg aaa gtg gac aaa gag tat     336
```

-continued

| | | |
|---|---|---|
| Asp Asp Ile Ser Lys Asn Met Ser Phe Leu Lys Val Asp Lys Glu Tyr<br>100 105 110 | | |
| gtg aaa gct tta ccc tcc cag ggt ctg agc tca tct gct gtt ttg gag<br>Val Lys Ala Leu Pro Ser Gln Gly Leu Ser Ser Ser Ala Val Leu Glu<br>115 120 125 | 384 | |
| aaa ctt aag gag tac agc tct atg gac gcc ttc tgg caa gag ggg aga<br>Lys Leu Lys Glu Tyr Ser Ser Met Asp Ala Phe Trp Gln Glu Gly Arg<br>130 135 140 | 432 | |
| gcc tct gga aca gtg tac agt ggg gag gag aag ctc act gag ctc ctt<br>Ala Ser Gly Thr Val Tyr Ser Gly Glu Glu Lys Leu Thr Glu Leu Leu<br>145 150 155 160 | 480 | |
| gtg aag gct tat gga gat ttt gca tgg agt aac ccc ctg cat cca gat<br>Val Lys Ala Tyr Gly Asp Phe Ala Trp Ser Asn Pro Leu His Pro Asp<br>165 170 175 | 528 | |
| atc ttc cca gga cta cgc aag ata gag gca gaa att gtg agg ata gct<br>Ile Phe Pro Gly Leu Arg Lys Ile Glu Ala Glu Ile Val Arg Ile Ala<br>180 185 190 | 576 | |
| tgt tcc ctg ttc aat ggg gga cca gat tcg tgt gga tgt gtg act tct<br>Cys Ser Leu Phe Asn Gly Gly Pro Asp Ser Cys Gly Cys Val Thr Ser<br>195 200 205 | 624 | |
| ggg gga aca gaa agc ata ctc atg gcc tgc aaa gca tat cgg gat ctg<br>Gly Gly Thr Glu Ser Ile Leu Met Ala Cys Lys Ala Tyr Arg Asp Leu<br>210 215 220 | 672 | |
| gcc ttt gag aag ggg atc aaa act cca gaa att gtg gct ccc caa agt<br>Ala Phe Glu Lys Gly Ile Lys Thr Pro Glu Ile Val Ala Pro Gln Ser<br>225 230 235 240 | 720 | |
| gcc cat gct gca ttt aac aaa gca gcc agt tac ttt ggg atg aag att<br>Ala His Ala Ala Phe Asn Lys Ala Ala Ser Tyr Phe Gly Met Lys Ile<br>245 250 255 | 768 | |
| gtg cgg gtc cca ttg acg aag atg atg gag gtg gat gtg agg gca atg<br>Val Arg Val Pro Leu Thr Lys Met Met Glu Val Asp Val Arg Ala Met<br>260 265 270 | 816 | |
| aga aga gct atc tcc agg aac act gcc atg ctc gtc tgt tct acc cca<br>Arg Arg Ala Ile Ser Arg Asn Thr Ala Met Leu Val Cys Ser Thr Pro<br>275 280 285 | 864 | |
| cag ttt cct cat ggt gta ata gat cct gtc cct gaa gtg gcc aag ctg<br>Gln Phe Pro His Gly Val Ile Asp Pro Val Pro Glu Val Ala Lys Leu<br>290 295 300 | 912 | |
| gct gtc aaa tac aaa ata ccc ctt cat gtc gac gct tgt ctg gga ggc<br>Ala Val Lys Tyr Lys Ile Pro Leu His Val Asp Ala Cys Leu Gly Gly<br>305 310 315 320 | 960 | |
| ttc ctc atc gtc ttt atg gag aaa gca gga tac cca ctg gag cac cca<br>Phe Leu Ile Val Phe Met Glu Lys Ala Gly Tyr Pro Leu Glu His Pro<br>325 330 335 | 1008 | |
| ttt gat ttc cgg gtg aaa ggt gta acc agc att tca gct gac acc cat<br>Phe Asp Phe Arg Val Lys Gly Val Thr Ser Ile Ser Ala Asp Thr His<br>340 345 350 | 1056 | |
| aag tat ggc tat gcc cca aaa ggc tca tca ttg gtg ttg tat agt gac<br>Lys Tyr Gly Tyr Ala Pro Lys Gly Ser Ser Leu Val Leu Tyr Ser Asp<br>355 360 365 | 1104 | |
| aag aag tac agg aac tat cag ttc ttc gtc gat aca gat tgg cag ggt<br>Lys Lys Tyr Arg Asn Tyr Gln Phe Phe Val Asp Thr Asp Trp Gln Gly<br>370 375 380 | 1152 | |
| ggc atc tat gct tcc cca acc atc gca ggc tca cgg cct ggt ggc att<br>Gly Ile Tyr Ala Ser Pro Thr Ile Ala Gly Ser Arg Pro Gly Gly Ile<br>385 390 395 400 | 1200 | |
| agc gca gcc tgt tgg gct gcc ttg atg cac ttc ggt gag aac ggc tat<br>Ser Ala Ala Cys Trp Ala Ala Leu Met His Phe Gly Glu Asn Gly Tyr<br>405 410 415 | 1248 | |
| gtt gaa gct acc aaa cag atc atc aaa act gct cgc ttc ctc aag tca | 1296 | |

-continued

```
                Val Glu Ala Thr Lys Gln Ile Ile Lys Thr Ala Arg Phe Leu Lys Ser
                            420                 425                 430 gaa ctg gaa aat atc aaa ggc atc ttt gtt ttt ggg aat ccc caa ttg         1344
Glu Leu Glu Asn Ile Lys Gly Ile Phe Val Phe Gly Asn Pro Gln Leu
            435                 440                 445 tca gtc att gct ctg gga tcc cgt gat ttt gac atc tac cga cta tca         1392
Ser Val Ile Ala Leu Gly Ser Arg Asp Phe Asp Ile Tyr Arg Leu Ser
        450                 455                 460 aac ctg atg act gct aag ggg tgg aac ttg aac cag ttg cag ttc cca         1440
Asn Leu Met Thr Ala Lys Gly Trp Asn Leu Asn Gln Leu Gln Phe Pro
465                 470                 475                 480 ccc agt att cat ttc tgc atc aca tta cta cac gcc cgg aaa cga gta         1488
Pro Ser Ile His Phe Cys Ile Thr Leu Leu His Ala Arg Lys Arg Val
                485                 490                 495 gct ata caa ttc cta aag gac att cga gaa tct gtc act caa atc atg         1536
Ala Ile Gln Phe Leu Lys Asp Ile Arg Glu Ser Val Thr Gln Ile Met
            500                 505                 510 aag aat cct aaa gcg aag acc aca gga atg ggt gcc atc tat ggc atg         1584
Lys Asn Pro Lys Ala Lys Thr Thr Gly Met Gly Ala Ile Tyr Gly Met
        515                 520                 525 gcc cag aca act gtt gac agg aat atg gtt gca gaa ttg tcc tca gtc         1632
Ala Gln Thr Thr Val Asp Arg Asn Met Val Ala Glu Leu Ser Ser Val
530                 535                 540 ttc ttg gac agc ttg tac agc acc gac act gtc acc cag ggc agc cag         1680
Phe Leu Asp Ser Leu Tyr Ser Thr Asp Thr Val Thr Gln Gly Ser Gln
545                 550                 555                 560 atg aat ggt tct cca aaa ccc cac tga                                     1707
Met Asn Gly Ser Pro Lys Pro His  *
                565

<210> SEQ ID NO 8
<211> LENGTH: 568
<212> TYPE: PRT
<213> ORGANISM: Homo sapiens

<400> SEQUENCE: 8

Met Pro Ser Thr Asp Leu Leu Met Leu Lys Ala Phe Glu Pro Tyr Leu
1               5                   10                  15

Glu Ile Leu Glu Val Tyr Ser Thr Lys Ala Lys Asn Tyr Val Asn Gly
            20                  25                  30

His Cys Thr Lys Tyr Glu Pro Trp Gln Leu Ile Ala Trp Ser Val Val
        35                  40                  45

Trp Thr Leu Leu Ile Val Trp Gly Tyr Glu Phe Val Phe Gln Pro Glu
    50                  55                  60

Ser Leu Trp Ser Arg Phe Lys Lys Cys Phe Lys Leu Thr Arg Lys
65                  70                  75                  80

Met Pro Ile Ile Gly Arg Lys Ile Gln Asp Lys Leu Asn Lys Thr Lys
                85                  90                  95

Asp Asp Ile Ser Lys Asn Met Ser Phe Leu Lys Val Asp Lys Glu Tyr
            100                 105                 110

Val Lys Ala Leu Pro Ser Gln Gly Leu Ser Ser Ala Val Leu Glu
        115                 120                 125

Lys Leu Lys Glu Tyr Ser Ser Met Asp Ala Phe Trp Gln Glu Gly Arg
130                 135                 140

Ala Ser Gly Thr Val Tyr Ser Gly Glu Glu Lys Leu Thr Glu Leu Leu
145                 150                 155                 160

Val Lys Ala Tyr Gly Asp Phe Ala Trp Ser Asn Pro Leu His Pro Asp
                165                 170                 175
```

```
Ile Phe Pro Gly Leu Arg Lys Ile Glu Ala Glu Ile Val Arg Ile Ala
            180                 185                 190

Cys Ser Leu Phe Asn Gly Gly Pro Asp Ser Cys Gly Cys Val Thr Ser
        195                 200                 205

Gly Gly Thr Glu Ser Ile Leu Met Ala Cys Lys Ala Tyr Arg Asp Leu
    210                 215                 220

Ala Phe Glu Lys Gly Ile Lys Thr Pro Glu Ile Val Ala Pro Gln Ser
225                 230                 235                 240

Ala His Ala Ala Phe Asn Lys Ala Ala Ser Tyr Phe Gly Met Lys Ile
                245                 250                 255

Val Arg Val Pro Leu Thr Lys Met Met Glu Val Asp Val Arg Ala Met
            260                 265                 270

Arg Arg Ala Ile Ser Arg Asn Thr Ala Met Leu Val Cys Ser Thr Pro
        275                 280                 285

Gln Phe Pro His Gly Val Ile Asp Pro Val Pro Glu Val Ala Lys Leu
    290                 295                 300

Ala Val Lys Tyr Lys Ile Pro Leu His Val Asp Ala Cys Leu Gly Gly
305                 310                 315                 320

Phe Leu Ile Val Phe Met Glu Lys Ala Gly Tyr Pro Leu Glu His Pro
                325                 330                 335

Phe Asp Phe Arg Val Lys Gly Val Thr Ser Ile Ser Ala Asp Thr His
            340                 345                 350

Lys Tyr Gly Tyr Ala Pro Lys Gly Ser Ser Leu Val Leu Tyr Ser Asp
        355                 360                 365

Lys Lys Tyr Arg Asn Tyr Gln Phe Phe Val Asp Thr Asp Trp Gln Gly
    370                 375                 380

Gly Ile Tyr Ala Ser Pro Thr Ile Ala Gly Ser Arg Pro Gly Gly Ile
385                 390                 395                 400

Ser Ala Ala Cys Trp Ala Ala Leu Met His Phe Gly Glu Asn Gly Tyr
                405                 410                 415

Val Glu Ala Thr Lys Gln Ile Ile Lys Thr Ala Arg Phe Leu Lys Ser
            420                 425                 430

Glu Leu Glu Asn Ile Lys Gly Ile Phe Val Phe Gly Asn Pro Gln Leu
        435                 440                 445

Ser Val Ile Ala Leu Gly Ser Arg Asp Phe Asp Ile Tyr Arg Leu Ser
    450                 455                 460

Asn Leu Met Thr Ala Lys Gly Trp Asn Leu Asn Gln Leu Gln Phe Pro
465                 470                 475                 480

Pro Ser Ile His Phe Cys Ile Thr Leu Leu His Ala Arg Lys Arg Val
                485                 490                 495

Ala Ile Gln Phe Leu Lys Asp Ile Arg Glu Ser Val Thr Gln Ile Met
            500                 505                 510

Lys Asn Pro Lys Ala Lys Thr Thr Gly Met Gly Ala Ile Tyr Gly Met
        515                 520                 525

Ala Gln Thr Thr Val Asp Arg Asn Met Val Ala Glu Leu Ser Ser Val
    530                 535                 540

Phe Leu Asp Ser Leu Tyr Ser Thr Asp Thr Val Thr Gln Gly Ser Gln
545                 550                 555                 560

Met Asn Gly Ser Pro Lys Pro His
                565

<210> SEQ ID NO 9
<211> LENGTH: 1707
<212> TYPE: DNA
<213> ORGANISM: Homo sapiens
```

<400> SEQUENCE: 9

```
atgcctagca cagaccttct gatgttgaag gcctttgagc cctacttaga gattttggaa      60
gtatactcca caaaagccaa gaattatgta aatggacatt gcaccaagta tgagccctgg     120
cagctaattg catggagtgt cgtgtggacc ctgctgatag tctggggata tgagtttgtc     180
ttccagccag agagtttatg gtcaaggttt aaaagaaat gttttaagct caccaggaag      240
atgcccatta ttggtcgtaa gattcaagac aagttgaaca agaccaagga tgatattagc     300
aagaacatgt cattcctgaa agtggacaaa gagtatgtga agctttacc ctcccagggt      360
ctgagctcat ctgctgtttt ggagaaactt aaggagtaca gctctatgga cgccttctgg     420
caagagggga gagcctctgg aacagtgtac agtggggagg agaagctcac tgagctcctt     480
gtgaaggctt atggagattt tgcatggagt aaccccctgc atccagatat cttcccagga     540
ctacgcaaga tagaggcaga aattgtgagg atagcttgtt ccctgttcaa tggggggacca    600
gattcgtgtg gatgtgtgac ttctggggga acagaaagca tactgatggc ctgcaaagca    660
tatcgggatc tggcctttga aaggggatc aaaactccag aaattgtggc tccccaaagt     720
gcccatgctg catttaacaa agcagccagt tactttggga tgaagattgt gcgggtccca    780
ttgacgaaga tgatggaggt ggatgtgcgg gcaatgagaa gagctatctc caggaacact    840
gccatgctcg tctgttctac cccacagttt cctcatggtg taatagatcc tgtccctgaa    900
gtggccaagc tggctgtcaa atacaaaata cccttcatg tcgacgcttg tctgggaggc    960
ttcctcatcg tctttatgga aaagcagga tacccactgg agcacccatt tgatttccgg    1020
gtgaaaggtg taaccagcat ttcagctgac accataagt atggctatgc cccaaaaggc    1080
tcatcattgg tgttgtatag tgacaagaag tacaggaact atcagttctt cgtcgataca    1140
gattggcagg gtggcatcta tgcttcccca accatcgcag gctcacggcc tggtggcatt    1200
agcgcagcct gttgggctgc cttgatgcac ttcggtgaga acggctatgt tgaagctacc    1260
aaacagatca tcaaaactgc tcgcttcctc aagtcagaac tggaaaatat caaaggcatc    1320
tttgttttg ggaatcccca attgtcagtc attgctctgg atcccgtga tttttgacatc    1380
taccgactat caaacctgat gactgctaag gggtggaact tgaaccagtt gcagttccca    1440
cccagtattc atttctgcat cacattacta cacgccgga acgagtagc tatacaattc       1500
ctaaaggaca ttcgagaatc tgtcactcaa atcatgaaga atcctaaagc gaagaccaca    1560
ggaatgggtg ccatctatgg catggcccag acaactgttg acaggaatat ggttgcagaa    1620
ttgtcctcag tcttcttgga cagcttgtac agcaccgaca ctgtcaccca gggcagccag    1680
atgaatggtt ctccaaaacc ccactga                                         1707
```

<210> SEQ ID NO 10
<211> LENGTH: 4
<212> TYPE: PRT
<213> ORGANISM: Artificial Sequence
<220> FEATURE:
<223> OTHER INFORMATION: Specifically recognized protein substrate for caspase-mediated cleavage

<400> SEQUENCE: 10

Tyr Val Ala Asp
 1

<210> SEQ ID NO 11
<211> LENGTH: 14
<212> TYPE: PRT
<213> ORGANISM: Mus musculus

```
<400> SEQUENCE: 11

Val Thr Gln Gly Asn Gln Met Asn Gly Ser Pro Lys Pro Arg
 1               5                   10
```

IMMUNOMODULATION BY ALTERING SPHINGOSINE 1-PHOSPHATE LYASE (SPL) ACTIVITY

STATEMENT OF GOVERNMENT INTEREST

This invention was made with government support under Grant No. CA77528 awarded by the National Institutes of Health. The government may have certain rights in this invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200116_407USPC_SEQUENCE_LISTING.txt. The text file is 48 KB, was created on Sep. 8, 2008 and is being submitted electronically via EFS-Web.

FIELD OF THE INVENTION

The present invention relates generally to compositions and methods for immune system regulation, and more particularly to therapeutic intervention to modulate immune function by influencing specific metabolic and signal transduction pathways that involve sphingolipids.

BACKGROUND OF THE INVENTION

Description of the Related Art

Sphingolipid metabolites and enzymes of sphingolipid metabolism play important roles in regulating cell migration, stress response, survival, differentiation, senescence, apoptosis, receptor signaling, and endocytosis in eukaryotic cells. These findings suggest molecular mechanisms by which sphingolipids may affect animal physiology and contribute to disease states. Mutations that result in failure or dysregulation of sphingolipid synthesis or catabolism are directly responsible for a number of human diseases, including hereditary sensory neuropathy type 1 and the group of lysosomal storage diseases called the sphingolipidoses (Bejaoui et al., 2001 *Nat Genet.* 27:261-2; Dawkins et al., 2001 *Nat Genet.* 27:309-12; Gable et al., 2002 *J Biol Chem* 277, 10194-200).

Sphingosine-1-phosphate (S1P) is an endogenous sphingolipid metabolite present in most mammalian cells and in serum, and is formed by phosphorylation of sphingosine mediated by the cellular enzyme sphingosine kinase (SK). Like other sphingolipid metabolites such as ceramide and sphingosine, S1P participates in specific signal transduction pathways. Many of the effects of S1P signaling, which include promotion of cellular proliferation, enhancement of migration, inhibition of apoptosis and stimulation of angiogenesis, influence the transformation, growth, drug resistance, vascularity and metastatic capacity of cancer cells. Several observations support the notion that sphingosine kinase (SK) and sphingosine-1-phosphate lyase (SPL) may be cancer related genes. First, the overexpression of SK in NIH3T3 fibroblasts leads to oncogenic transformation as determined by the ability of transfected cells to form foci in vitro and to form fibrosarcomas in NOD/SCID mice. Second, human SPL was cloned and mapped to 10q21, a chromosomal region frequently deleted in a variety of human cancers.

As noted above, S1P mediates a variety of cell signaling activities and is believed to do so by interacting specifically with multiple cellular receptors, including a family of G protein-coupled receptors. One such receptor, $S1P_1$, has been shown to interact with a synthetic prodrug, FTY720, only after phosphorylation of the prodrug by SK yields the drug in its active form, FTY720P.

FTY720 is an immunosuppressive agent that modulates lymphocyte trafficking and prevents allograft rejection (Budde et al., (2002) *J Am Soc Nephrol* 13, 1073-1083; Brinkmann, V. (2004) *Yonsei Med J* 45, 991-997). FTY720 treatment stimulates lymphocyte homing to peripheral lymph nodes and Peyer's patches, resulting in prolonged survival of allograft tissues and both prevention and treatment of various autoimmune diseases in animal models (Brinkmann, V., and Lynch, K. R. (2002) *Curr Opin Immunol* 14, 569-575). FTY720 induces numerous effects on the immune system including inhibited egress of both naïve and activated CD4+, CD8+ and B lymphocytes from peripheral lymphoid organs and thymus, cysteinyl leukotriene-dependent T cell chemotaxis to lymph nodes, peripheral blood lymphopenia, egress of lymphocytes from the spleen, displacement of B cells from the marginal zone of the spleen, decreased $\beta 1$ integrin expression on marginal zone B cells, homing of hematopoietic progenitor cells to the bone marrow, and decreased vascular permeability (Chiba et al., (1998) *J Immunol* 160, 5037-5044; Matloubian et al, (2004) *Nature* 427, 355-360; Mandala et al., (2002) *Science* 296, 346-349; Xie et al., (2003) *J Immunol* 170, 3662-3670; Vora et al., (2005) *J Leukocyte Biology* 78, 1-10; Honig et al., (2003) *J Clin Invest* 111, 627-637; Sanchez et al., (2003) *J Biol Chem* 278, 47281-47290; Kimura et al., (2004) *Blood* ___; Halin et al., (2005) *Blood* epub ahead of print). Importantly, while FTY720 prevents the migration of lymphocytes to allogeneic graft tissue and other sites of inflammation, it does not diminish the activation, proliferation or effector functions of B and T lymphocytes in response to antigen stimulation (Pinschewer et al., (2000) *J Immunol* 164, 5761-5770). Toxicities associated with FTY720 are limited and distinct from those of other immunosuppressive drugs, which makes FTY720 a candidate for combination immunosuppressive transplantation regimens.

FTY720 was rationally designed based on chemical modifications of myriocin, a naturally occurring sphingoid base analog that causes immunosuppression by interrupting sphingolipid metabolism (Fujita et al., (1994) *J Antibiot* (Tokyo) 47, 208-215). FTY720 is phosphorylated in vivo (Billich et al., (2003) *J Biol Chem* 278, 47408-47415), and as noted above, the phosphorylated form of the drug acts as an agonist for a family of G protein coupled receptors that recognize the sphingolipid metabolite (and SK product) sphingosine 1-phosphate (S1P) as the endogenous ligand (Mandala et al., (2002) *Science* 296, 346-349; Brinkmann et al., (2002) *J Biol Chem* 277, 21453-21457). Genetic and biochemical evidence suggests that FTY720P-induced activation of the $S1P_1$ receptor is primarily responsible for the effect of the drug on lymphocytes (Matloubian et al, (2004) *Nature* 427, 355-360). While FTY720P is an $S1P_1$ receptor agonist, exposure to the drug also results in receptor internalization and downregulation on lymphocytes, which is thought to be the mechanism of action, since reconstitution of mice with hematopoietic progenitors or lymphocytes lacking $S1P_1$ expression emulates the effects of FTY720 treatment on lymphocyte egress and trafficking (Allende et al., (2004) *J Biol Chem* 279, 15396-15401; Graler et al., (2004) *Faseb J* 18, 551-553).

Intracellular S1P levels are regulated by SK-mediated synthesis of S1P from sphingosine, and by S1P degradation by lipid phosphatases and by the enzyme SPL, a pyridoxal 5′-phosphate-dependent enzyme that resides in the ER and is responsible for the irreversible degradation of S1P to ethanolamine phosphate and hexadecimal (Spiegel et al., (2000) *FEBS Lett* 476, 55-57). Given the pleiotropic effects of FTY720 and of SIP, however, there is clearly a need for an improved ability to modulate immune function. As described herein, the present invention addresses this need and offers other related advantages.

BRIEF SUMMARY OF THE INVENTION

According to certain embodiments of the present invention, there is provided a method of modulating immune function in a subject, comprising administering to the subject an agent that alters sphingosine-1-phosphate lyase (SPL) activity, and thereby modulating immune function. In certain further embodiments modulating immune function comprises reducing or preventing tissue inflammation in the subject, and in certain other further embodiments modulating immune function comprises treating or preventing a condition that is selected from transplant graft rejection, autoimmune disease and allergy, and in certain other further embodiments modulating immune function comprises altering proliferation or survival of an immune system cell. In a still further embodiment the immune system cell is a lymphocyte or a hematopoietic cell of lymphoid lineage.

In another embodiment the agent that alters sphingosine-1-phosphate lyase (SPL) activity is capable of decreasing SPL activity, and in a further embodiment the agent that is capable of decreasing SPL activity binds to SPL. In another further embodiment the agent that is capable of decreasing SPL activity causes a decreased expression level of SPL. In another further embodiment the agent that causes a decreased expression level of SPL is selected from (a) an antisense polynucleotide that specifically hybridizes to a nucleic acid molecule that encodes a SPL polypeptide, (b) a ribozyme that specifically cleaves a nucleic acid molecule that encodes a SPL polypeptide, (c) a small interfering RNA that is capable of interfering with a nucleic acid molecule that encodes a SPL polypeptide, (d) an agent that alters activity of a regulatory element that is operably linked to a nucleic acid molecule that encodes a SPL polypeptide, and (e) an antibody that specifically binds to a translated product of a nucleic acid molecule that encodes a SPL polypeptide, wherein the nucleic acid molecule that encodes a SPL polypeptide is selected from (i) a nucleic acid molecule comprising a nucleotide sequence as set forth in SEQ ID NO:1 (nucleic acid encoding human SPL polypeptide) or a complementary sequence thereto, or as set forth in SEQ ID NO:3 (nucleic acid encoding murine SPL polypeptide) or a complementary sequence thereto, (ii) a nucleic acid molecule comprising a nucleotide sequence that hybridizes under moderately stringent conditions to the nucleic acid molecule of (i) and that encodes a polypeptide having sphingosine-1-phosphate lyase (SPL) activity, and (iii) a nucleic acid molecule that encodes a SPL polypeptide which comprises an amino acid sequence as set forth in SEQ ID NO:2 (human SPL) or a portion of SEQ ID NO:2 having sphingosine-1-phosphate lyase (SPL) activity, or as set forth in SEQ ID NO:4 (murine SPL) or a portion of SEQ ID NO:4 having sphingosine-1-phosphate lyase (SPL) activity.

In another embodiment the agent that alters sphingosine-1-phosphate lyase (SPL) activity is not FTY720 or myriocin. In another embodiment the agent that alters sphingosine-1-phosphate lyase (SPL) activity is selected from deoxypyridoxine, $C_8$-cyclopropenylceramide and $C_{16}$-cyclopropenylceramide. In another embodiment the agent that alters sphingosine-1-phosphate lyase (SPL) activity alters activity of a regulatory element that is operably linked to a nucleic acid molecule that encodes a SPL polypeptide, wherein the regulatory element comprises a GATA transcription factor-binding motif. In another embodiment the agent that alters sphingosine-1-phosphate lyase (SPL) activity is selected from (a) a mutated form of a nucleic acid molecule that encodes a SPL polypeptide wherein the mutated form encodes a dominant negative mutant SPL polypeptide, or a complementary polynucleotide thereto, and (b) a dominant negative mutant SPL polypeptide encoded by (a), wherein the nucleic acid molecule that encodes a SPL polypeptide is selected from the group consisting of (i) a nucleic acid molecule comprising a nucleotide sequence as set forth in SEQ ID NO:1 or a complementary sequence thereto, or as set forth in SEQ ID NO:3 or a complementary sequence thereto, (ii) a nucleic acid molecule comprising a nucleotide sequence that hybridizes under moderately stringent conditions to the nucleic acid molecule of (i) and that encodes a polypeptide having sphingosine-1-phosphate lyase (SPL) activity, and (iii) a nucleic acid molecule that encodes a SPL polypeptide which comprises an amino acid sequence as set forth in SEQ ID NO:2 or a portion of SEQ ID NO:2 having sphingosine-1-phosphate lyase (SPL) activity, or as set forth in SEQ ID NO:4 or a portion of SEQ ID NO:4 having sphingosine-1-phosphate lyase (SPL) activity.

These and other aspects of the present invention will become apparent upon reference to the following detailed description and attached drawings. All references (including websites and including the following patents and patent applications: U.S. Pat. No. 6,423,527; U.S. Pat. No. 6,569,666; U.S. Pat. No. 6,495,359; U.S. application Ser. No. 10/053, 510; U.S. application Ser. No. 10/286,175; U.S. application Ser. No. 10/197,073; U.S. application Ser. No. 10/348,052; U.S. application Ser. No. 10/622,011; PCT/US2003/01739) disclosed herein are hereby incorporated by reference in their entireties as if each was incorporated individually.

DETAILED DESCRIPTION OF THE INVENTION

Figure 1A:
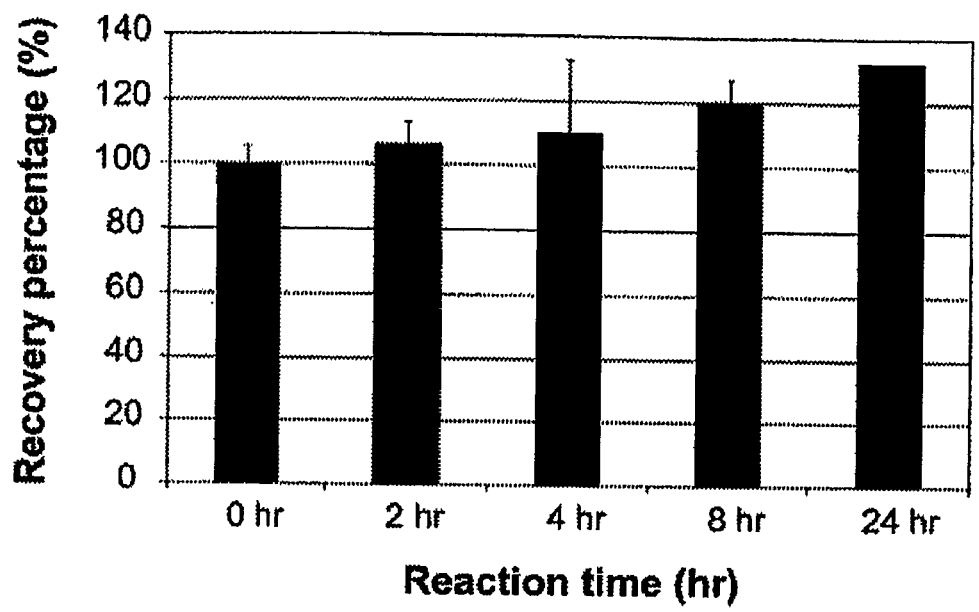
FIG. 1 shows stability of FTY720-P in the presence of SPL. (A) Twenty nanomoles of FTY720-P were incubated with SPL enzyme for 0-24 hours under standard SPL reaction conditions in the absence of dihydrosphingosine 1-phosphate substrate. At the indicated times the reaction was stopped, and FTY720-P was recovered and quantified by HPLC. (B) Twenty nanomoles of S1P were incubated with extracts from cells overexpressing SPL for 0-24 hours, or alternatively, with extracts from cells containing pcDNA3.0 vector control which had no appreciable SPL activity (PC) for 2 hours. S1P was recovered and quantified by HPLC.

The present invention relates to the surprising discovery that altering (i.e., increasing or decreasing in a statistically significant manner) SPL activity results in altered immune function, and thus in its various embodiments provides methods and compositions for modulating (i.e., altering) immune function. Accordingly there is provided, in the form of SPL, a target for therapeutic intervention to modulate immune function in a subject. It will be appreciated that in certain preferred embodiments, alteration of SPL by decreasing SPL activity to modulate immune function, whether by directly or indirectly inhibiting SPL catalytic degradation of S1P, or by substantially impairing (i.e., decreasing in a statistically significant manner) SPL expression levels, desirably influences one or more particular immunological parameters to confer clinical benefits.

As described herein, the unexpected immunomodulatory role of SPL was identified through determination that the immunosuppressive agent FTY720 can directly inhibit SPL activity. As described above, FTY720 was previously believed to exert physiological effects only as a S1P receptor ($S1P_1$) agonist following its specific conversion by SK to the phosphorylated form of the drug, FTY720P. Hence, only in view of the present application can it be appreciated that pharmacological intervention by way of altering SPL activity results in useful therapeutic modalities to modulate immune function. For example, SPL inhibitors (alone or in combination with other immunomodulatory agents) may usefully promote immune suppression to prevent rejection of solid organ or bone marrow grafts in transplantation medicine, and/or to prevent sequelae of autoimmune diseases.

Immune function is mediated by immune system cells which include, but are not limited to, cells of hematopoietic origin including cells at various stages of differentiation within myeloid and lymphoid lineages and which may (but need not) express one or more types of lineage-specific, subpopulation-specific and/or functional cell surface molecules including well known differentiation markers, as may be found, for instance, on T lymphocytes, B lymphocytes, NK cells, monocytes, macrophages, dendritic cells, neutrophils, basophils, eosinophils, mast cells, erythrocytes, and precursors, progenitors (e.g., hematopoietic stem cells), quiescent, activated and mature forms of such cells. (see, e.g., *Leucocyte Typing VII,* 2002, Mason et al. (Eds.), Oxford Univ. Press, London) Other immune system cells may include cells of non-hematopoietic origin that are capable of mediating immune functions, for example, endothelial cells, keratinocytes, fibroblasts, osteoclasts, epithelial cells and other cells. Immune system cells may also include cells that mediate cytotoxic or cytostatic events, or endocytic, phagocytic, or pinocytotic events, or that effect induction of apoptosis, or that effect microbial immunity or neutralization of microbial infection, or cells that mediate allergic, inflammatory, hypersensitivity and/or autoimmune reactions. According to certain preferred embodiments described herein, an immune system cell may be a lymphocyte such as a T lymphocyte or a B lymphocyte or another hematopoietic cell of lymphoid lineage.

As will be known to persons having ordinary skill in the art, immune function includes an immune response, which may be any active alteration of the immune status of a host, and which may include any alteration in the structure or function of one or more tissues, organs, cells or molecules that participate in maintenance and/or regulation of host immune status. Typically, immune responses may be detected by any of a variety of well known parameters, including but not limited to in vivo or in vitro determination of: soluble immunoglobulins or antibodies; soluble mediators such as cytokines, lymphokines, chemokines, hormones, growth factors and the like as well as other soluble small peptide, carbohydrate, nucleotide and/or lipid mediators; cellular activation state changes as determined by altered functional or structural properties of cells of the immune system, for example cell proliferation, altered motility, induction of specialized activities such as specific gene expression or cytolytic behavior; cellular differentiation by cells of the immune system, including altered surface antigen expression profiles or the onset of apoptosis (programmed cell death); or any other criterion by which the presence of an immune response may be detected.

Immune responses may often be regarded, for instance, as discrimination between self and non-self structures by the cells and tissues of a host's immune system at the molecular and cellular levels, but the invention should not be so limited. For example, immune responses may also include immune system state changes that result from immune recognition of self molecules, cells or tissues, as may accompany any number of normal conditions such as typical regulation of immune system components, or as may be present in pathological conditions such as the inappropriate autoimmune responses observed in autoimmune and degenerative diseases. As another example, in addition to induction by up-regulation of particular immune system activities (such as antibody and/or cytokine production, or activation of cell mediated immunity) immune responses may also include suppression, attenuation or any other down-regulation of detectable immunity, which may be the consequence of the antigen selected, the route of antigen administration, specific tolerance induction or other factors.

Certain embodiments of the present invention relate to modulating an immune function in a subject by administering an agent that alters SPL activity, for treating or preventing allergy. Allergic immune response mechanisms are well known in the art and include an antigen (e.g., allergen)-specific component such as an immunoglobulin (e.g., IgE), as well as the cells and mediators which comprise sequelae to allergen-immunoglobulin (e.g., IgE) encounters (e.g., Ott et al., 2000 *J. Allerg. Clin. Immunol.* 106:429; Barnes, 2000*J. Allerg. Clin. Immunol.* 106:5; Togias, 2000 *J. Allerg. Clin. Immunol.* 105:S599; Akdis et al., 2000 *Int. Arch. Allerg. Immunol.* 121:261; Beach, 2000 *Occup. Med.* 15:455).

According to certain other embodiments provided herein, immune function may be modulated in a subject by administering an agent that alters SPL activity, for treating or preventing transplantation graft rejection. Such grafts may, by way of non-limiting examples, be solid organ grafts or may alternatively be hematopoietic grafts, and graft rejection may be determined according to accepted criteria in the relevant medical arts, including classic host rejection of, e.g., allograft or xenograft tissue, and also including, e.g., graft-versus-host disease (GVHD) as may, for instance, accompany bone marrow transplantation following myeloablation in a therapeutic regimen for treating cancer.

In certain embodiments the present invention relates to a method of modulating immune function in a subject that comprises administering an agent that alters SPL activity, for purposes of treating or preventing an autoimmune disease, i.e., a disease, disorder or condition wherein a host immune system generates an inappropriate anti-"self" immune reaction. Such an autoimmune response may be characterized by the production of anti-"self" reactive antibodies (autoantibodies) and/or by induction of antigen-specific or non-specific cell-mediated and/or soluble mediator-driven autoimmune reactions, including inflammatory cascades. Examples of autoimmune diseases for which modulation of immune function may be beneficially applied according to certain invention embodiments include autoimmune diabetes (e.g., Type I diabetes mellitus), rheumatoid arthritis, systemic lupus erythematosus, multiple sclerosis, Crohn's disease, and other autoimmune conditions.

Immune function modulating agents may be used to modulate, modify or otherwise alter (e.g., increase or decrease) cellular responses such as immune system cell proliferation, differentiation and survival, in a variety of contexts, both in vivo and in vitro. Thus, modulation of an immune function may in certain embodiments pertain to altering the proliferation or survival of one or a plurality of immune system cells. A wide variety of methodologies for determining cellular proliferation is known in the art and may have application to certain embodiments disclosed herein for purposes of identifying altered (e.g., increased or decreased with statistical significance) immune system cell proliferation in a subject or in a biological sample from a subject. Such techniques include, but are not limited to, cytological, biochemical, histochemical, radiochemical or immunochemical staining of cells for characteristic proliferation-associated (e.g., metaphase chromosome stains, DNA stains such as propidium iodide, $^3$H-thymidine incorporation, MTT staining) or cell cycle markers (e.g., Rabinovitch, 1994 *Meths. Cell Biol.* 41:263-296) or the like.

Cells that are suspected of undergoing apoptosis may be examined for morphological, permeability or other changes that are indicative of an apoptotic state. For example by way of illustration and not limitation, apoptosis in many cell types may cause altered morphological appearance such as plasma membrane blebbing, cell shape change, loss of substrate adhesion properties or other morphological changes that can be readily detected by a person having ordinary skill in the art, for example by using light microscopy. As another example, cells undergoing apoptosis may exhibit fragmentation and disintegration of chromosomes, which may be apparent by microscopy and/or through the use of DNA-specific or chromatin-specific dyes that are known in the art, including fluorescent dyes. Such cells may also exhibit altered plasma membrane permeability properties as may be readily detected through the use of vital dyes (e.g., propidium iodide, trypan blue) or by the detection of lactate dehydrogenase leakage into the extracellular milieu. Another readily practiced method for detecting apoptotic cells relates to detection of altered plasma membrane outer leaflet phospholipid composition in such cells, as determined, for instance, by quantification of phosphatidylserine exteriorization in the plasma membrane using detectably labeled annexin V (e.g., Fadok et al., *J. Immunol.* 148:2207, 1992). These and other means for detecting apoptotic cells by morphologic criteria, altered plasma membrane permeability and related changes will be apparent to those familiar with the art.

Apopotosis may also be determined by an assay for induction of specific protease activity in any member of a family of apoptosis-activated proteases known as the caspases (see, e.g., Green et al., 1998 *Science* 281:1309). Those having ordinary skill in the art will be readily familiar with methods for determining caspase activity, for example by determination of caspase-mediated cleavage of specifically recognized protein substrates. These substrates may include, for example, poly-(ADP-ribose) polymerase (PARP) or other naturally occurring or synthetic peptides and proteins cleaved by caspases that are known in the art (see, e.g., Ellerby et al., 1997 *J. Neurosci.* 17:6165). The synthetic peptide Z-Tyr-Val-Ala-Asp-AFC (SEQ ID NO:10), wherein "Z" indicates a benzoyl carbonyl moiety and AFC indicates 7-amino-4-trifluoromethylcoumarin (Kluck et al., 1997 *Science* 275:1132; Nicholson et al., 1995 *Nature* 376:37), is one such substrate. Other non-limiting examples of substrates include nuclear proteins such as U1-70 kDa and DNA-PKcs (Rosen and Casciola-Rosen, 1997 *J. Cell. Biochem.* 64:50; Cohen, 1997 *Biochem. J.* 326:1). Cellular apoptosis may also be detected by determination of cytochrome c that has escaped from mitochondria in apoptotic cells (e.g., Liu et al., *Cell* 86:147, 1996). Such detection of cytochrome c may be performed spectrophotometrically, immunochemically or by other well established methods for determining the presence of a specific protein. Alternatively, apoptosis or necrosis of the cell, and/or modulation of the functioning of the cell cycle within the cell, may be detected using art-established criteria. (See, e.g., Ashkenazi et al., 1998 *Science,* 281:1305; Thornberry et al., 1998 *Science* 281:1312; Evan et al., 1998 *Science* 281:1317; Adams et al., 1998 *Science* 281:1322; and references cited therein; see also, e.g., Wyllie, 1980 *Nature* 284:555; Arends et al., 1990 *Am. J. Pathol.* 136:593.) Persons having ordinary skill in the art will readily appreciate that there may be other suitable techniques for quantifying apoptosis.

Agents that alter SPL activity are described herein and additional suitable agents for use according to the present embodiments may be identified according to routine methodologies, such as those described in the herein incorporated references. For instance, methods of detecting SPL activity, and of screening compound libraries for agents that alter SPL activity, including polynucleotide sequences for the production of nucleic acid molecules that encode SPL polypeptides and the production of SPL polypeptides therefrom, are disclosed in U.S. application Ser. No. 10/348,052, U.S. application Ser. No. 10/622,011, and PCT/US2003/01739, including in publications cited therein (e.g., Van Veldhoven and Mannaerts, 1991 *J. Biol. Chem.* 266:12502-07) and elsewhere. For embodiments that relate to molecular biology methodologies, compositions and methods well known to those of ordinary skill in the art are described for example, in Sambrook et al., *Molecular Cloning: A Laboratory Manual*, Cold Spring Harbor Laboratories, Cold Spring Harbor, N.Y., 1989; Ausubel et al. (1993 *Current Protocols in Molecular Biology*, Greene Publ. Assoc. Inc. & John Wiley & Sons, Inc., Boston, Mass.); Maniatis et al. (1982 Molecular Cloning, Cold Spring Harbor Laboratory, Plainview, N.Y.) and elsewhere. Certain embodiments as provided herein expressly contemplate a method of modulating immune function in a subject that comprises administering an agent that alters SPL activity wherein the agent is not FTY720 or myriocin, but certain other embodiments are not so limited and may include embodiments wherein a method of modulating immune function comprises administering FTY720 and/or myriocin, optionally in combination with one or more additional agents, such as an agent that alters SPL activity and/or an agent that alters SK activity and/or an agent that alters a level of S1P or an interaction between S1P and an S1P receptor such as $S1P_1$ (or another G protein-coupled S1P receptor), or another agent.

In certain other embodiments a method of modulating immune function in a subject is expressly contemplated that comprises administering an agent that alters SPL activity wherein the agent is at least one of deoxypyridoxine, $C_8$-cyclopropenylceramide and $C_{16}$-cyclopropenylceramide, each of which has been shown to be capable of altering SPL activity (see, e.g., Triola et al., 2004 *Mol. Pharmacol.* 66:1671; see also Matreya LLC 2005 Catalog (Pleasant Gap, Pa.), Cat. Nos. 1886 and 1887).

As also provided herein, certain contemplated embodiments relate to a method of modulating immune function in a subject by administering an agent that decreases SPL activity, which in certain embodiments may involve an agent that decreases SPL activity by directly binding to SPL, while in certain other embodiments an agent that decreases SPL activity may do so indirectly, for example, by interacting with other cellular molecular components that exert an effect on SPL activity. Certain contemplated embodiments relate to an agent that is capable of decreasing SPL activity by causing a decreased expression level of SPL.

Compositions and methods directed to altering (e.g., increasing or decreasing with statistical significance) SPL expression levels are described in U.S. Pat. No. 6,423,527; U.S. Pat. No. 6,569,666; U.S. Pat. No. 6,495,359; U.S. application Ser. No. 10/053,510; U.S. application Ser. No. 10/286,175; U.S. application Ser. No. 10/197,073; U.S. application Ser. No. 10/348,052; U.S. application Ser. No. 10/622,011; and PCT/US2003/01739, wherein can be found abundant disclosure describing nucleic acid molecules that encode SPL polypeptides, including SPL-encoding polynucleotides (and nucleotides that hybridize thereto under moderately stringent conditions, which may be, e.g., prewashing in a solution of 5×SSC, 0.5% SDS, 1.0 mM EDTA (pH 8.0); hybridizing at 50-65° C., 5×SSC, overnight; followed by washing twice at 65° C. for 20 minutes with each of 2×, 0.5× and 0.2×SSC containing 0.1% SDS) and encoded SPL polypeptide sequences, and wherein also can be found description of antibodies that specifically bind to a translated polypeptide product of an SPL-encoding nucleic acid molecule. Certain embodiments contemplated herein thus include the use of all or a portion of such an SPL-encoding polynucleotide and/or a polynucleotide that hybridizes thereto under moderately stringent conditions, for example, a polynucleotide that comprises all or a portion of the nucleotide sequence set forth in any one of SEQ ID NOS:1, 3, 5, 7 and 9.

According to certain related embodiments, an agent that causes a decreased SPL expression level may be an antisense polynucleotide that specifically hybridizes to a nucleic acid molecule that encodes a SPL polypeptide, a ribozyme that specifically cleaves a nucleic acid molecule that encodes a SPL polypeptide, a small interfering RNA that is capable of interfering with a nucleic acid molecule that encodes a SPL polypeptide, or an agent that alters activity of a regulatory element that is operably linked to a nucleic acid molecule that encodes a SPL polypeptide. As disclosed herein and known to the art, such nucleic acid sequence-based agents can be readily prepared using routine methodologies A polynucleotide that is complementary to at least a portion of a coding sequence (e.g., an antisense polynucleotide or a ribozyme) may thus be used to modulate SPL-encoding gene expression. Identification of oligonucleotides and ribozymes for use as antisense agents, and DNA encoding genes for their targeted delivery, involve methods well known in the art. For example, the desirable properties, lengths and other characteristics of such oligonucleotides are well known.

Antisense oligonucleotides are typically designed to resist degradation by endogenous nucleolytic enzymes by using such linkages as: phosphorothioate, methylphosphonate, sulfone, sulfate, ketyl, phosphorodithioate, phosphoramidate, phosphate esters, and other such linkages (see, e.g., Agrwal et al., *Tetrahedron Lett.* 28:3539-3542 (1987); Miller et al., *J. Am. Chem. Soc.* 93:6657-6665 (1971); Stec et al., *Tetrahedron Lett.* 26:2191-2194 (1985); Moody et al., *Nucl. Acids Res.* 12:4769-4782 (1989); Uznanski et al., *Nucl. Acids Res.* (1989); Letsinger et al., *Tetrahedron* 40:137-143 (1984); Eckstein, *Annu. Rev. Biochem.* 54:367-402 (1985); Eckstein, *Trends Biol. Sci.* 14:97-100 (1989); Stein In: *Oligodeoxynucleotides. Antisense Inhibitors of Gene Expression*, Cohen, Ed, Macmillan Press, London, pp. 97-117 (1989); Jager et al., *Biochemistry* 27:7237-7246 (1988)).

Antisense polynucleotides are oligonucleotides that bind in a sequence-specific manner to nucleic acids, such as mRNA or DNA. When bound to mRNA that has complementary sequences, antisense prevents translation of the mRNA (see, e.g., U.S. Pat. No. 5,168,053 to Altman et al.; U.S. Pat. No. 5,190,931 to Inouye, U.S. Pat. No. 5,135,917 to Burch; U.S. Pat. No. 5,087,617 to Smith and Clusel et al. (1993) *Nucl. Acids Res.* 21:3405-3411, which describes dumbbell antisense oligonucleotides). Triplex molecules refer to single DNA strands that bind duplex DNA forming a colinear triplex molecule, thereby preventing transcription (see, e.g., U.S. Pat. No. 5,176,996 to Hogan et al., which describes methods for making synthetic oligonucleotides that bind to target sites on duplex DNA).

Particularly useful antisense nucleotides and triplex molecules are molecules that are complementary to or bind the sense strand of DNA or mRNA that encodes a SPL polypeptide or a protein mediating any other process related to expression of endogenous SPL, such that inhibition of translation of mRNA encoding the SPL polypeptide is effected. cDNA constructs that can be transcribed into antisense RNA may also be introduced into cells or tissues to facilitate the production of antisense RNA. Antisense technology can be used to control gene expression through interference with binding of polymerases, transcription factors or other regulatory molecules (see Gee et al., In Huber and Carr, *Molecular and Immunologic Approaches*, Futura Publishing Co. (Mt. Kisco, N.Y.; 1994)). Alternatively, an antisense molecule may be designed to hybridize with a control region of a SPL-encoding gene (e.g., promoter, enhancer or transcription initiation site), and block transcription of the gene; or to block translation by inhibiting binding of a transcript to ribosomes.

The present invention also contemplates use of SPL-encoding nucleic acid sequence-specific ribozymes. A ribozyme is an RNA molecule that specifically cleaves RNA substrates, such as mRNA, resulting in specific inhibition or interference with cellular gene expression. There are at least five known classes of ribozymes involved in the cleavage and/or ligation of RNA chains. Ribozymes can be specifically targeted to any RNA transcript and can catalytically cleave such transcripts (see, e.g., U.S. Pat. No. 5,272,262; U.S. Pat. No. 5,144,019; and U.S. Pat. Nos. 5,168,053, 5,180,818, 5,116,742 and 5,093,246 to Cech et al.). Any SPL mRNA-specific ribozyme, or a nucleic acid encoding such a ribozyme, may be delivered to a host cell to effect inhibition of SPL gene expression. Ribozymes may therefore be delivered to the host cells by DNA encoding the ribozyme linked to a eukaryotic promoter, such as a eukaryotic viral promoter, such that upon introduction into the nucleus, the ribozyme will be directly transcribed. Particularly useful sequence regions of a SPL-encoding mRNA for use as a ribozyme target can be found using routine sequence alignment tools known to the art such as BLAST or MegAlign, and may preferably be sequence stretches that are unique to the SPL-encoding mRNA relative to other transcribed sequences that may be present in a particular cell. In one preferred example, a ribozyme may be designed and constructed such that it is targeted to bind to a region of SPL-encoding mRNA that encodes a portion of the human SPL polypeptide containing the lysine residue found at amino acid position 353 therein, but the invention is not so limited and other ribozymes targeted to other regions of SPL-encoding mRNA are also contemplated.

Any polynucleotide may be further modified to increase stability in vivo. Possible modifications include, but are not limited to, the addition of flanking sequences at the 5' and/or 3' ends; the use of phosphorothioate or 2' O-methyl rather than phosphodiester linkages in the backbone; and/or the inclusion of nontraditional bases such as inosine, queosine and wybutosine, as well as acetyl-methyl-, thio- and other modified forms of adenine, cytidine, guanine, thymine and uridine.

RNA interference (RNAi) is a polynucleotide sequence-specific, post-transcriptional gene silencing mechanism effected by double-stranded RNA that results in degradation of a specific messenger RNA (mRNA), thereby reducing the expression of a desired target polypeptide encoded by the mRNA (see, e.g., WO 99/32619; WO 01/75164; U.S. Pat. No. 6,506,559; Fire et al., Nature 391:806-11 (1998); Sharp, Genes Dev. 13:139-41 (1999); Elbashir et al. Nature 411:494-98 (2001); Harborth et al., J. Cell Sci. 114:4557-65 (2001)). "Small interfering RNA" (siRNA) or DNP-RNA polynucleotides that interfere with expression of specific polypeptides in higher eukaryotes such as mammals (including humans) have been considered (e.g., Karagiannis and El-Osta, 2005 Cancer Gene Ther. May 2005, PMID: 15891770; Chen et al., 2005 Drug Discov. Today 10:587; Scherr et al., 2005 Curr. Opin. Drug Discov. Devel. 8:262; Tomari and Zamore, 2005 Genes Dev. 19:517; see also, e.g., Tuschl, 2001 Chembiochem. 2:239-245; Sharp, 2001 Genes Dev. 15:485; Bernstein et al., 2001 RNA 7:1509; Zamore, 2002 Science 296:1265; Plasterk, 2002 Science 296:1263; Zamore 2001 Nat. Struct. Biol. 8:746; Matzke et al., 2001 Science 293:1080; Scadden et al., 2001 EMBO Rep. 2:1107; Hutvagner et al., Curr. Opin. Gen. Dev. 12:225-32 (2002); Elbashir et al., 2001; Nykänen et al., Cell 107:309-21 (2001); Bass, Cell 101:235-38 (2000)); Zamore et al., Cell 101:25-33 (2000)). Transfection of human and other mammalian cells with double-stranded RNAs of about 18-27 nucleotide base pairs in length interferes in a sequence-specific manner with expression of particular polypeptides encoded by messenger RNAs (mRNA) containing corresponding nucleotide sequences (WO 01/75164; Elbashir et al., 2001; Elbashir et al., Genes Dev. 15:188-200 (2001)); Harborth et al., J. Cell Sci. 114:4557-65 (2001); Carthew et al., Curr. Opin. Cell Biol. 13:244-48 (2001); Mailand et al., Nature Cell Biol. Advance Online Publication (Mar. 18, 2002); Mailand et al. 2002 Nature Cell Biol. 4:317). SPL-specific siRNA constructs are available and have been obtained from Dharmacon (Lafayette, Colo.). In certain non-limiting embodiments double-stranded RNAs for use in RNAi may have, for example, 17, 18, 19, 20, 21, 22, 23, 24, 25, 26, 27, 28, 29, 30, 31, 32 or more nucleotide base pairs.

As noted above, in certain embodiments the agent that causes a decreased SPL expression level may alter activity of a regulatory element that is operably linked to a nucleic acid molecule that encodes a SPL polypeptide. According to a related embodiment the regulatory element comprises a GATA transcription factor-binding motif (Oskouian et al., 2005 J. Biol. Chem. 280:18403-410). By way of representative example and not limitation, these and related embodiments contemplate suitable agents that are capable of down-regulating SPL activity by suppressing or repressing transcription of SPL-encoding genes, which agents can be readily identified using art-accepted methodologies to screen for functional blockers of SPL gene transcription. For instance, Oskouian et al. (2005) describe regulation of the human SPL gene by a GATA transcription factor that interacts with an upstream regulatory element, as characterized using a reporter gene transcriptional run-off assay that can be readily adapted to screen for functional inhibitors of SPL gene expression. Using such an approach, agents capable of causing decreased SPL expression levels may be identified from compound libraries such as libraries of synthetic (e.g., combinatorial chemistry) small molecules, or natural products libraries, or recombinant expression libraries, or other sources.

Certain other embodiments as disclosed herein contemplate a method of modulating immune function in a subject that comprises administering an agent that alters sphingosine-1-phosphate lyase (SPL) activity, wherein the agent is selected from (a) a mutated form of a nucleic acid molecule that encodes a SPL polypeptide wherein the mutated form encodes a dominant negative mutant SPL polypeptide, or a complementary polynucleotide thereto, and (b) a dominant negative mutant SPL polypeptide encoded by (a). The nucleic acid molecule that encodes a SPL polypeptide is described above and in several above-referenced patents and patent applications, e.g., U.S. application Ser. No. 10/348,052, U.S. application Ser. No. 10/622,011, and PCT/US2003/01739, including in publications cited therein (e.g., Van Veldhoven and Mannaerts, 1991 J. Biol. Chem. 266:12502-07), as are compositions and methods for introducing mutations (see, e.g., Sambrook et al., 1989; Ausubel et al., 1993; Maniatis et al., 1982). Principles and practices directed to functional inactivation of a desired target gene using a dominant negative mutation are described in Herskowitz et al. (1987 Nature 329:219-222) and in Perlmutter et al. (1996 Curr. Opin. Immunol. 8:285-290). Without wishing to be bound by theory, according to these and related embodiments a dominant negative mutant SPL may be engineered and functionally identified using routine methodologies as described herein and in the cited references, such that introduction of the dominant negative mutant (e.g., by administering a mutated SPL-encoding nucleic acid molecule by suitable art-accepted methodologies such as transfection, electroporation, biolistics, naked DNA, plasmid, viral vector, liposomal delivery or other suitable means, or by administering a mutant SPL polypeptide) in a manner and for a time sufficient to obtain an immune system cell having the dominant negative SPL, results in competition for substrate (e.g., S1P) between wildtype (endogenous) SPL and the dominant negative mutant SPL, thereby effectively decreasing the effective level of SPL activity in the cell.

Therapeutic Methods

One or more agents that alter SPL activity as provided herein and/or as identified according to the above-described methods may also be used to modulate immune function in a subject. As used herein, a "subject" may be any mammal, including a human, and may be afflicted with a condition associated with inappropriate or undesired immunological activity or may be free of any detectable disease, disorder or condition of abnormal immune function. Accordingly, the treatment may be of an existing disease or may be prophylactic. Conditions for which it may be desirable to modulate immune function include any disorder associated with cell proliferation, including inflammation, transplant graft rejection (e.g., allograft rejection or graft-versus-host disease (GVHD)), autoimmune diseases, allergy or other conditions.

For administration to a patient, one or more agents that alter SPL activity are generally formulated as a pharmaceutical composition. A pharmaceutical composition may be a sterile aqueous or non-aqueous solution, suspension or emulsion, which additionally comprises a physiologically acceptable carrier (i.e., a non-toxic material that does not interfere with the activity of the active ingredient). Such compositions may be in the form of a solid, liquid or gas (aerosol). Alternatively, compositions of the present invention may be formulated as a lyophilizate or compounds may be encapsulated within liposomes using well known technology. Pharmaceutical compositions within the scope of the present invention may also contain other components, which may be biologically active or inactive. Such components include, but are not limited to, buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, stabilizers, dyes, flavoring agents, and suspending agents and/or preservatives.

Any suitable carrier known to those of ordinary skill in the art may be employed in the pharmaceutical compositions of the present invention. Carriers for therapeutic use are well known, and are described, for example, in *Remingtons Pharmaceutical Sciences*, Mack Publishing Co. (A. R. Gennaro ed. 1985). In general, the type of carrier is selected based on the mode of administration. Pharmaceutical compositions may be formulated for any appropriate manner of administration, including, for example, topical, oral, nasal, intrathecal, rectal, vaginal, sublingual or parenteral administration, including subcutaneous, intravenous, intramuscular, intrasternal, intracavernous, intrameatal or intraurethral injection or infusion. For parenteral administration, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, kaolin, glycerin, starch dextrins, sodium alginate, carboxymethylcellulose, ethyl cellulose, glucose, sucrose and/or magnesium carbonate, may be employed.

A pharmaceutical composition (e.g., for oral administration or delivery by injection) may be in the form of a liquid (e.g., an elixir, syrup, solution, emulsion or suspension). A liquid pharmaceutical composition may include, for example, one or more of the following: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. A parenteral preparation can be enclosed in ampoules, disposable syringes or multiple dose vials made of glass or plastic. The use of physiological saline is preferred, and an injectable pharmaceutical composition is preferably sterile.

The compositions described herein may be formulated for sustained release (i.e., a formulation such as a capsule or sponge that effects a slow release of compound following administration). Such compositions may generally be prepared using well known technology and administered by, for example, oral, rectal or subcutaneous implantation, or by implantation at the desired target site. Sustained-release formulations may contain an agent dispersed in a carrier matrix and/or contained within a reservoir surrounded by a rate controlling membrane. Carriers for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated or prevented.

Within a pharmaceutical composition, a therapeutic agent comprising one or more agents that alter SPL activity may be linked to any of a variety of compounds. For example, such an agent may be linked to a targeting moiety (e.g., a monoclonal or polygonal antibody, a protein or a liposome) that facilitates the delivery of the agent to the target site. As used herein, a "targeting moiety" may be any substance (such as a compound or cell) that, when linked to an agent enhances the transport of the agent to a target cell or tissue, thereby increasing the local concentration of the agent. Targeting moieties include antibodies or fragments thereof, receptors, ligands and other molecules that bind to cells of, or in the vicinity of, the target tissue. An antibody targeting agent may be an intact (whole) molecule, a fragment thereof, or a functional equivalent thereof. Examples of antibody fragments are $F(ab')_2$, Fab', Fab and F[v] fragments, which may be produced by conventional methods or by genetic or protein engineering. Linkage is generally covalent and may be achieved by, for example, direct condensation or other reactions, or by way of bi- or multi-functional linkers. Targeting moieties may be selected based on the cell(s) or tissue(s) toward which the agent is expected to exert a therapeutic benefit.

Pharmaceutical compositions may be administered in a manner appropriate to the disease or condition to be treated (or prevented). An appropriate dosage and a suitable duration and frequency of administration will be determined by such factors as the condition of the patient, the type and severity of the patient's disease, the particular form of the active ingredient and the method of administration. In general, an appropriate dosage and treatment regimen provides the agent(s) in an amount sufficient to provide therapeutic and/or prophylactic benefit (e.g., an improved clinical outcome, such as more frequent complete or partial remissions, or longer disease-free and/or overall survival, or a lessening of symptom severity). For prophylactic use, a dose should be sufficient to prevent, delay the onset of or diminish the severity of a disease associated with cell proliferation.

Optimal dosages may generally be determined using experimental models and/or clinical trials. In general, the amount of an agent that alters SPL activity present in a dose, ranges from about 0.01 μg to about 100 μg per kg of host, typically from about 0.1 μg to about 10 μg. The use of the minimum dosage that is sufficient to provide effective therapy is usually preferred. Patients may generally be monitored for therapeutic or prophylactic effectiveness using assays suitable for the condition being treated or prevented, which will be familiar to those having ordinary skill in the art. Suitable dose sizes will vary with the size of the patient, but will typically range from about 10 mL to about 500 mL for 10-60 kg animal.

The following Examples are offered by way of illustration and not limitation.

EXAMPLES

Example 1

Experimental Procedures

Materials: FTY720 and FTY720-P were provided by Volker Brinkmann of Novartis (Basel, Switzerland). C17 and C18 sphingosines, PSo and S1Ps were obtained from Biomol Research Laboratories, Inc. (Plymouth Meeting, Pa.). [4,5$^3$H]-D-erythro-DHS 1-P was obtained from American Radiolabeled Chemicals, Inc. (St. Louis, Mo.). All other chemicals including 1-butanol and o-phthalaldehyde (OPA) were purchased from Sigma/Aldrich (St. Louis, Mo.). GT11 (C8 and C16 analogues) was obtained from Matreya LLC (Pleasant Gap, Pa.).

FTY720-P metabolism: Whole cell extracts of HEK293 cells stably overexpressing human SPL were prepared as previously described (Reiss et al., (2004) *J Biol Chem* 279, 1281-1290). These extracts contained approximately 700 picomoles/mg protein/minute of SPL activity. Twenty nanomoles FTY720-P were suspended in SPL reaction buffer (Van Veldhoven et al., (1991) *J Biol Chem* 266, 12502-12507), and 25 microliters of whole cell extract were added to initiate the reaction. At various time points, reaction was stopped by addition of a 2 ml mixture of chloroform and methanol (2:1 v/v), 1 ml of 1M KCl, 0.1 ml concentrated HCl. Sample was mixed by vortexing and centrifuged at 1200 rpm for 5 min. Organic phase was collected, dried down using a speed vac and resuspended in methanol. After derivatization with OPA, the sample was injected onto the HPLC for quantification. The HPLC analysis was conducted using a Beckman (Torrance, Calif., USA) system Gold 125 solvent module with a Spectra-Physics SP8410 fluorescence detector and a C18 (2) Luna 3 μm, 75×4.6 mm column from Phenomenex (CA). The mobile phase was methanol:10 mM phosphate buffer pH 7.2:1M tetrabutylammonium dihydrogen phosphate (TBAP) in water=83:16:1, v/v/v and the flow rate was 1 ml/min. The calculation of the FTY720-P in each sample was based on the integration of the peaks of interest and the comparison of the OPA derivative of untreated FTY720-P. For comparison, 10 nanomoles S1P were incubated with extracts from HEK293 cells overexpressing SPL or HEK293 cells containing vector, and extraction of S1P was performed as for FTY720. Recovery of S1P was determined by HPLC quantitation, as described below for S1P measurements in mouse tissues.

Confirmation of FTY720-P by LCMS: Samples corresponding to FTY720-P peak identified on HPLC were evaluated by LCMS to confirm FTY720-P by mass analysis. Twenty microliters of sample were injected into the LCMS and mass spectrum scans from 300 to 500 m/z and specific ions m/Z 388 and 410 were quantified for FTY720-P. A reverse phase C18 column from Phenomenex (2.1 mm×15 cm) was used. Two mobile phases were used: solution A is water:methanol:acetic acid (69:30:1) containing 5 mM ammonium acetate and solution B is methanol:acetic acid (99:1) containing 5 mM ammonium acetate. The program for these two mobile phases was started with 50% A and B, continued for 2 min and then B was increased to 100% in 6 min, continued for 5 min in 100% B and finally decreased B back to 50% in 2 min. The flow rate was 0.3 ml/min. The retention time was 11.2 min.

Drug treatments and leukocyte/lymphocyte counts: Four-week old FVB or C3H mice were obtained from Charles River Laboratories (Wilmington, Mass.). Animals were maintained in a pathogen-free facility in microisolator cages. Mice were anaesthetized with isoflurane inhalation, and a single dose of FTY720 (at 1 or 3 mg/kg) or GT11 (at 1, 10 or 100 mg/kg) in sterile water was injected intraperitoneally at time zero. Blood counts were determined by Coulter counter (Coulter Instruments, Hialeah, Fla.) and by manual differential counting. Mice were euthanized by $CO_2$ inhalation at various time points post-injection, followed by tissue harvest. All animal studies were performed in accordance with approved CHORI IACUC protocols.

SPL enzyme assay: Tissues were homogenized by sonication in 9 volumes of ice-cold homogenization buffer (5 mM MOPS pH 7.5, 1 mM DTT, 1 mM EDTA, 0.25 M sucrose, and 5 micrograms/ml each chymostatin, leupeptin, pepstatin A and antipain). SPL assays were conducted using 50 micrograms protein per assay and radioactive [4,5 $^3$H]DHS1P substrate, as described previously (Reiss et al., (2004) *J Biol Chem* 279, 1281-1290). For in vitro FTY720 and FTY720-P experiments, drug was incubated with whole cell extracts prepared from HEK293 cells infected with an adenoviral vector expressing human SPL. These extracts contained approximately 200 picomoles/mg protein/minute SPL activity. Drug was incubated with extracts for 30 minutes, followed by addition of extracts to reaction buffer and substrate to initiate the reaction.

S1P measurements: S1P was isolated by two-phase lipid extraction, derivatized with OPA and quantitated by HPLC essentially as described (Jiang et al, (2004) *Proc Natl Acad Sci USA* 101, 17825-17830; Fyrst et al., (2004) *J Lipid Res* 45, 54-62; Caligan et al., (2000) *Anal. Biochem.* 281, 36-44). All tissues were weighed prior to snap freezing in liquid nitrogen and were stored at −100° C. until processing. One nanomole of C17-S1P and PSo were added as internal standards before homogenization of tissues. Lipids were extracted with 1 ml mixture of chloroform and methanol (1:2 ratio). Samples were incubated at room temperature with sonication for 3 hours and then dried by speed vac. One ml of 0.1N NaOH in methanol was added for 1 hour at 37° C. to achieve hydrolysis. After addition of 4 ml chloroform and 4 ml 1M KCl, samples were mixed and phases separated by centrifugation. The organic phase was collected and dried for sphingosine determination. The aqueous phase was mixed with 300 μl concentrated HCl and 6 ml chloroform. The phases were separated by centrifugation, and the organic phase was collected and dried for S1P determination. All samples for S1P determination were re-dissolved in methanol. After derivation with OPA, samples were injected onto HPLC for quantification. The mobile phase was methanol:10 mM phosphate buffer (pH 7.2):1M tetrabutylammonium dihydrogen phosphate (TBAP) in water=83:16:1, v/v/v and the flow rate was 1 ml/min.

SPL expression: To evaluate the effect of FTY720 and FTY720-P on SPL gene expression, HEK293 cells were treated for 30 minutes with 3 μM of either drug, followed by transfection with pSPL-BamHI, a human SPL-luciferase reporter construct. After 48 hours, reporter expression was determined by luciferase activity as described (Oskouian et al., (2005) *J Biol Chem* 280, 18403-18410)). Western blotting of mouse tissue extracts was performed using a 1:2000 dilution of polyclonal sera raised against the murine SPL C-terminal peptide: ($NH_2$)—V-T-Q-G-N-Q-M-N-G-S—P—K—P—R—(COOH). [SEQ ID NO:11]

Cellular Immune Functions—Mitogen Induced Lymphoproliferation: Spleen and thymus tissues were harvested from wild type C3H mice, and cell suspensions were prepared as described previously (Mishell et al., (1980) in *Selected Methods in Cellular Immunology* (Mishell, B., and Shiigi, S., eds), pp. 3-27, WH Freeman and Company, San Francisco). Cells were dispersed in sterile medium in 96 well microtiter plates (Falcon) at a concentration of 1×10⁶ cells/ml for spleen and 5×10⁶ cells/ml for thymus. Cells were incubated in the presence or absence of GT11 for 24 hours at 37 C in 5% CO2, followed by treatment with 1 or 10 µg/ml LPS or vehicle control (BSS). Cell proliferation was determined after 48 and 72 hours using the Cell Titer 96 Non-Radioactive Cell Proliferation Assay from Promega (Mannheim, Germany), according to the manufacturer's instructions.

Example 2

FTY720 but not FTY720P Inhibits SPL Activity

SPL does not catabolize FTY720-P-FTY720 demonstrated a long elimination half-life after single dose administration (Brinkmann, (2004) *Yonsei Med J* 45, 991-997). Known routes of drug metabolism included conversion to FTY720-P by SK, and omega oxidation of the octyl side chain, followed by beta oxidation.

Figure 1B:
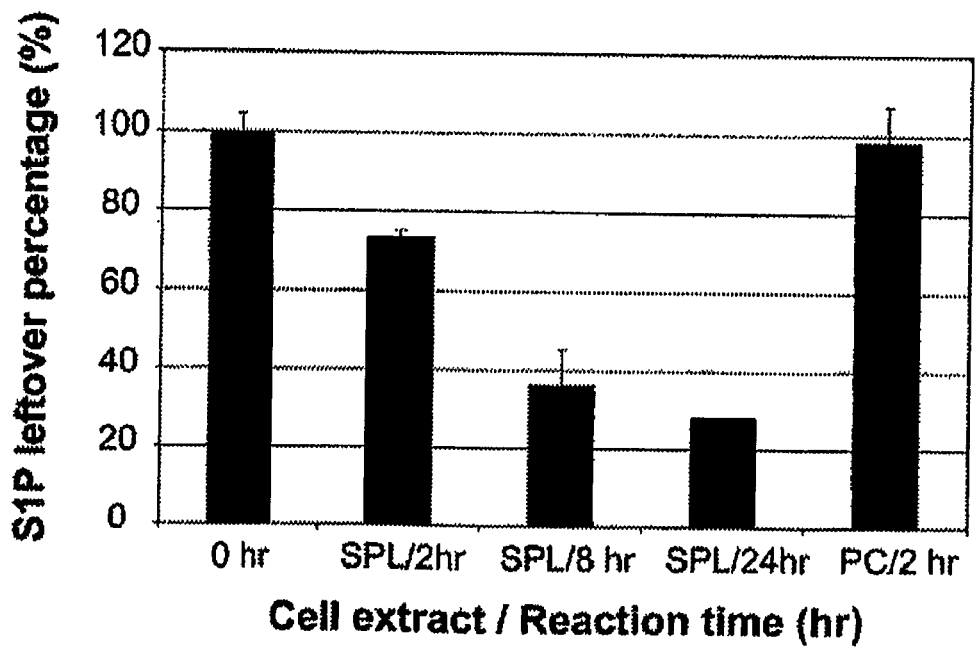

This Example describes testing of whether FTY720 might function as a substrate for SPL, which recognizes phosphorylated long chain bases of varying chain length, hydroxylation and saturation. First, FTY720-P was incubated under standard SPL assay conditions with HEK293 cells previously determined to demonstrate high levels of SPL activity by virtue of their stable expression of a human SPL-GFP fusion protein. Incubation proceeded for various lengths of time, after which FTY720-P was recovered by two-phase lipid extraction, derivatized with the fluorescent compound OPA and quantitated by HPLC. As shown in FIG. 1A, FTY720-P remained stable for up to 24 hours in the presence of SPL. In contrast, S1P levels diminished under the same conditions (FIG. 1B).

S1P levels following FTY720-P exposure in HEK293 cells that overexpressed SPL (Reiss et al., 2004 *J Biol Chem* 279: 1281) were also compared to control green fluorescent protein (GFP)-transfectants, and S1P levels diminished in the SPL overexpressors but not in the GFP-expressing control cells. These results indicated that FTY720-P did not serve as a substrate for SPL under standard conditions.

Figure 2:
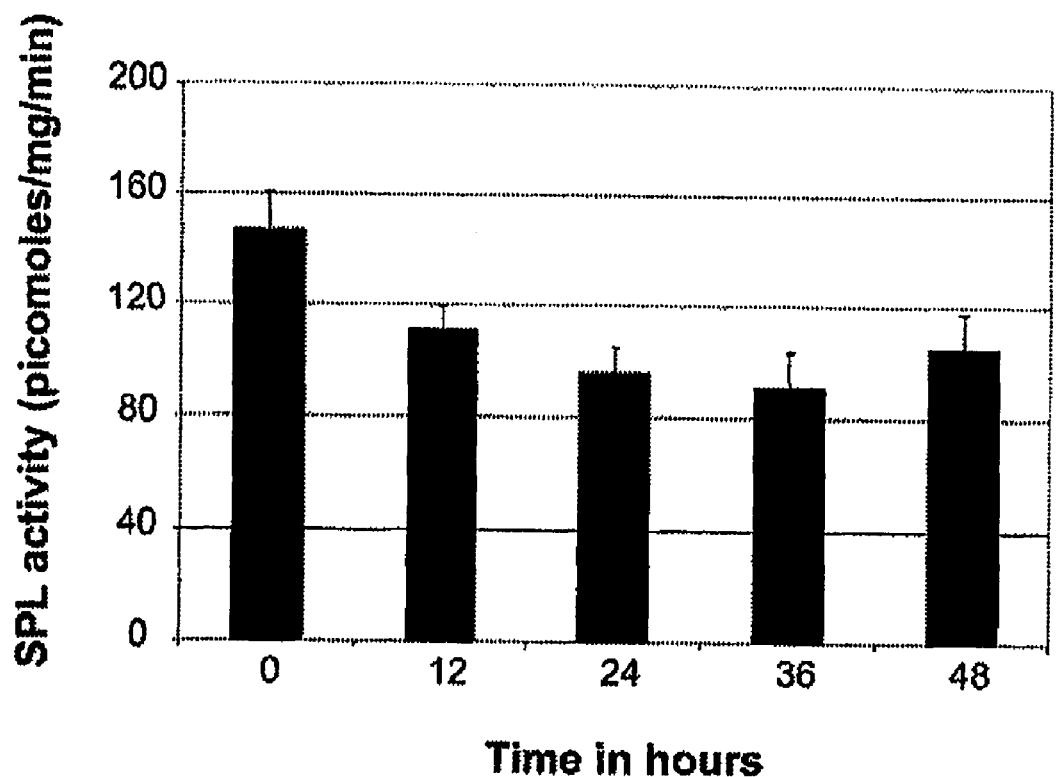
FIG. 2 shows inhibition of SPL activity by FTY720 in vivo. One mg/kg FTY720 was administered by peritoneal injection to FVB mice at time zero. Mice were euthanized at the indicated times, and SPL activity in thymic tissue was determined.

Inhibition of SPL by FTY720 in vivo—The effect on SPL enzyme activity of FTY720 administration was tested. Four-week old female FVB mice were given 1 mg/kg FTY720 by intraperitoneal injection, and tissue SPL activity in thymus was assessed over time. As shown in FIG. 2, inhibition of SPL was noted as early as 12 hours after FTY720 treatment, peaked at 36 hours at approximately 40% inhibition, and began to reverse by 48 hours. SPL inhibition occurred concomitantly with lymphopenia, and was consistent with the timing of lymphopenia reported previously (Chiba et al., (1998) *J Immunol* 160, 5037-5044) (Table 1).

TABLE 1

Lymphocyte counts after FTY720 treatment

| Time in Hours | Lymphocytes (1000/µL) | SD |
|---|---|---|
| 0 | 4.5 | 1.15 |
| 24 | 2.2 | 0.52 |
| 48 | 3.2 | 0.56 |
| 72 | 2.0 | 0.37 |

To address whether the inhibition of SPL activity in homogenates of tissues isolated from FTY720 treated animals was reversible, tissue SPL activity was measured in the presence of increasing amounts of non-radiolabeled DHS1P substrate. Enzyme inhibition (21%) that was observed in tissues from animals treated with FTY720 for 24 hours was partially overcome (reduced to 14% inhibition) by a 2-fold increase in unlabeled substrate, whereas the level of inhibition in the presence of 40 nmol unlabeled substrate (25%) was similar to that observed with 10 nmol of substrate (standard assay conditions).

In separate experiments, SPL expression in vivo was detected in the thymus and in intestinal inflammatory cells by immunohistochemistry. Briefly, polyclonal rabbit anti-murine SPL antisera (see, e.g., U.S. Pat. No. 7,041,291) were diluted 1:200 in 0.5% ovalbumin/PBS and incubated with murine thymic and intestinal tissue sections from normal 129sv/C57BL/6 mice and, as a control, from SPL-deficient embryonic stem cell $SPL^{-/-}$ ($Sgpl^{-/-}$) knockout mice generated in the 129sv/C57BL/6 background according to established methodologies (Chen et al., 2004 *Nature Genetics* 36:304). Sections were then rinsed and developed using biotinylated anti-rabbit immunoglobulin (Vector Laboratories, Burlingame, Calif.) and the EliteABC™ kit (Vector) according to the manufacturer's instructions. No staining was observed in tissues from the $SPL^{-/-}$ ($Sgpl^{-/-}$) knockout mice, confirming the specificity of the antibodies in the rabbit anti-murine SPL antisera. In the normal ($SPL^{+/+}$) animals, however, SPL was localized immunohistochemically to thymic epithelium in thymus sections, and to inflammatory cells apparently including lymphocytes in intestinal tissue sections.

Figure 3A:
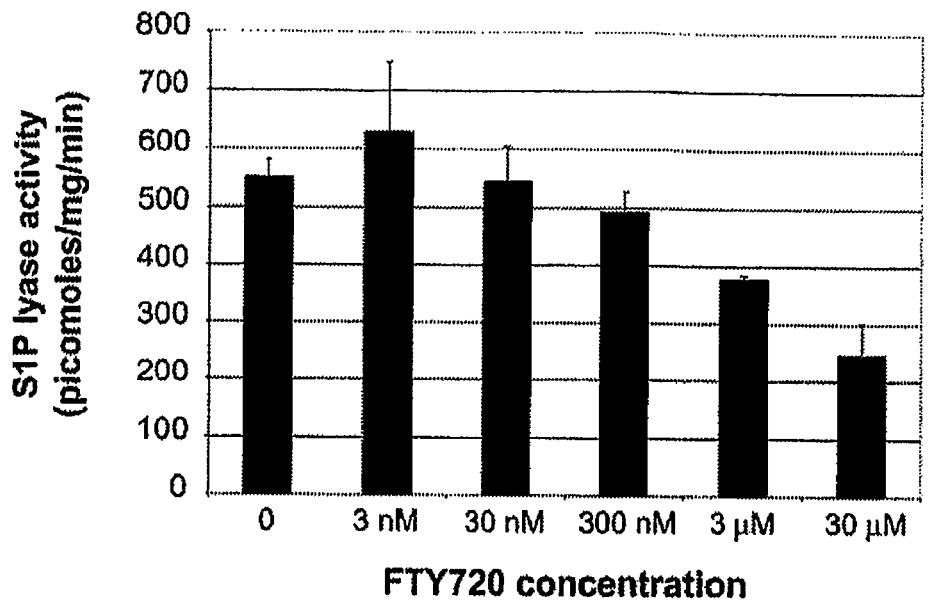
FIG. 3 shows inhibition of SPL activity by FTY720 in vitro. Various concentrations of FTY720 or its phosphorylated derivative (FTY720P) were incubated for 30 minutes on ice with whole cell extracts containing high SPL activity by virtue of a human SPL adenoviral expression construct. SPL activity was determined. (A) FTY720; (B) FTY720-P.
Figure 3B:
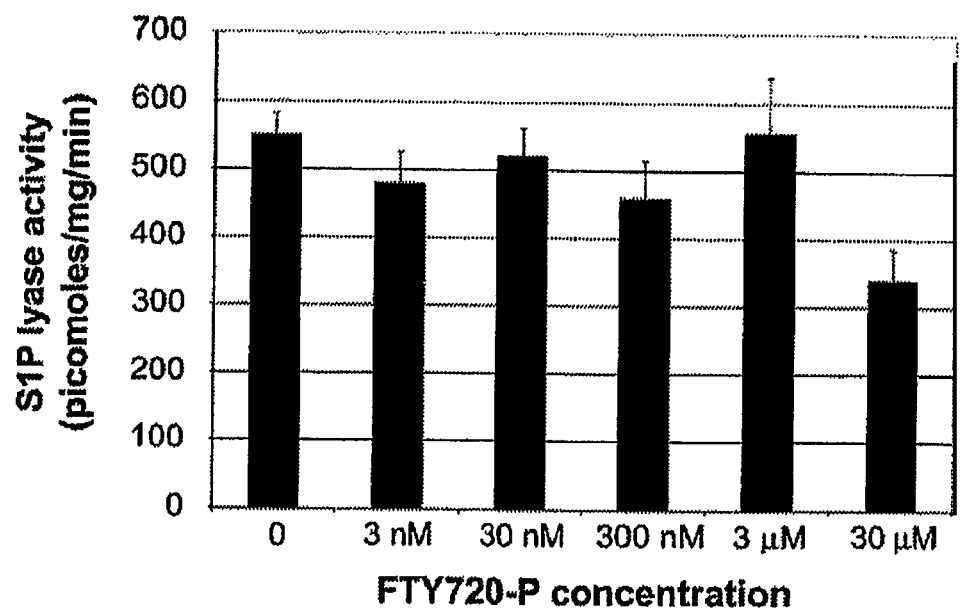

Inhibition of SPL activity by FTY720 in vitro—To determine whether the effect of FTY720 on SPL activity was due to a direct interaction between the SPL enzyme and the long chain base analog in either its phosphorylated or unphosphorylated form, whole cell extracts were prepared from HEK293 cells expressing high levels of SPL by virtue of an SPL-adenoviral construct and incubated with varying concentrations of FTY720 or FTY720-P. As shown in FIG. 3A, FTY720 inhibited SPL activity in vitro in a dose-dependent fashion, with effects occurring as low as 300 nM and maximal effect observed at 30 µM. In contrast, FTY720-P was inhibitory only at 30 µM, and the effect was not dose-dependent. Although treatment with FTY720 was associated with low (nanomolar) circulating drug levels, it was possible that local concentrations within cells and subcellular compartments may have been considerably higher, since FTY720 has been reported to be actively transported into cells by the actions of drug transporters that recognize long chain bases (Honig et al., (2003) *J Clin Invest* 111, 627-637).

Example 3

FTY720 Effects on SPL In Vivo

Figure 4A:
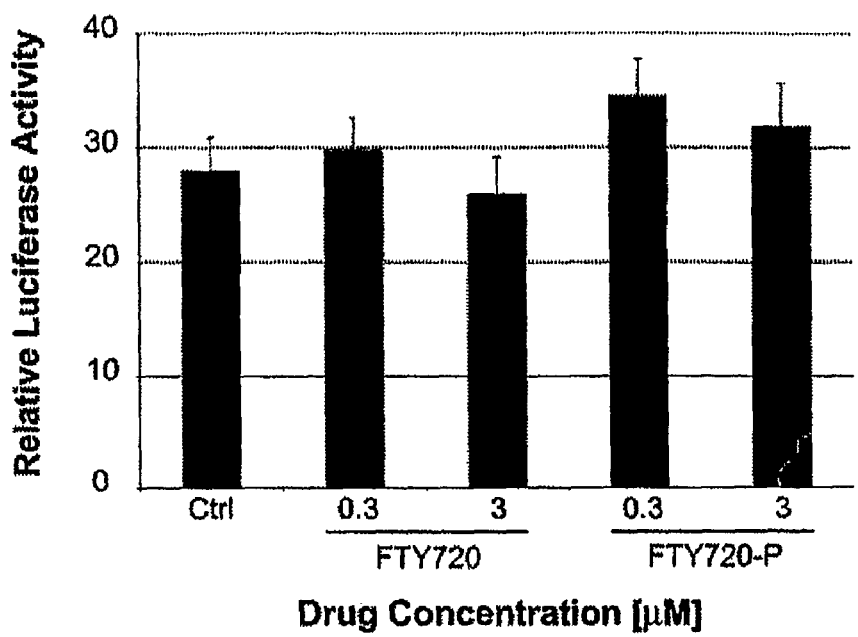
FIG. 4 shows SPL expression was not affected by FTY720 or FTY720P. (A) SPL gene expression. HEK293 cells were co-transfected with a human SPL luciferase reporter construct and the sea pansy luciferase reporter as a control for transfection efficiency. Twenty-four hours after transfection, cells were treated with 0.3 µM FTY720, 3.0 µM FTY720 or vehicle and incubated for another 24 hours at 37° C. Luciferase activity was then determined as a measure of expression, as described in Experimental Methods. Values shown are luciferase activity normalized to sea pansy luciferase; (B) SPL protein expression. Thymic extracts from control mice (time 0) and mice treated with FTY720 for 24 hours were evaluated for SPL protein expression by immunoblotting. Actin was used as a loading control.
Figure 4B:
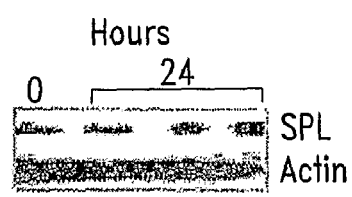

FTY720 effect on SPL gene or protein expression—SPL gene expression was inducible by GATA transcription factors (Oskouian et al., (2005) *J Biol Chem* 280, 18403-18410) and other physiological conditions, including DNA damage, hypoxia, and other stress conditions (unpublished observations). Therefore, SPL expression was examined in the tissues of mice treated with FTY720, as well as in cell lines exposed to FTY720. Neither SPL gene expression as determined by a SPL-luciferase reporter system (FIG. 4A) nor tissue SPL protein expression as determined by immunoblotting (FIG. 4B) appeared to be affected by FTY720 treatment at doses that inhibited enzyme activity. These studies confirmed that the major effect of the drug on SPL activity is through a post-translational mechanism.

FTY720 administration minimally affects tissue S1P levels—SK is known to be responsible for S1P synthesis, whereas SPL and S1P phosphatases are responsible for S1P catabolism. Since FTY720 interacts with both SK and SPL and may potentially influence the efficiency of both S1P synthesis and degradation, the sum effect of FTY270 administration on tissue S1P levels was determined. FTY720 treatment was associated with a slight increase in thymic tissue S1P at 36 hours, followed by a return to baseline levels by 48 hours (Table 2). Dihydrosphingosine-1-P levels also remained stable throughout 48 hours of treatment (data not shown). S1P levels increased somewhat more dramatically in splenic tissue after FTY720 treatment (Table 2). DHS1P levels remained stable throughout 48 hours of treatment. These findings indicated that, despite potential competition with sphingosine by FTY720 as a substrate for sphingosine kinases, tissue S1P levels did not decrease and may have increased transiently. According to non-limiting theory, simultaneous inhibition of SPL may account for the stability of tissue S1P levels in response to drug treatment.

TABLE 2

S1P levels in murine tissue after FTY720 treatment

| Time in Hours | S1P (thymus)[1] | S.D. | | |
|---|---|---|---|---|
| 0 | 3375.50 | 1358.26 | | |
| 24 | 3000.69 | 1382.10 | | |
| 36 | 3917.48 | 184.67 | | |
| 48 | 3194.45 | 1162.69 | | |

| Time in Hours | S1P (thymus)[1] | S.D. | S1P (spleen)[1] | S.D. |
|---|---|---|---|---|
| 0 | 3152.00 | 1053.90 | 10229.65 | 357.02 |
| 24 | 3000.69 | 1382.10 | 15121.31 | 4009.99 |
| 36 | 3917.48 | 184.67 | 18482.30 | 302.34 |
| 48 | 3194.45 | 1162.69 | 12365.84 | 128.65 |

Values are picomoles per gram of wet weight tissue; n = 4 animals per time point (S.D., standard deviation)

In summary, these studies demonstrated that FTY720 inhibited the activity of SPL, the major enzyme responsible for irreversibly removing S1P from the sphingosine-S1P cycle. This effect was observed in vivo at therapeutic doses of the drug and concomitant with lymphopenia and in vitro at somewhat higher concentrations. Further according to non-limiting theory, inhibition of SPL by FTY720 may have limited FTY720 cytotoxicity by preventing S1P depletion during conversion of the drug to its phosphorylated form.

Figure 5:
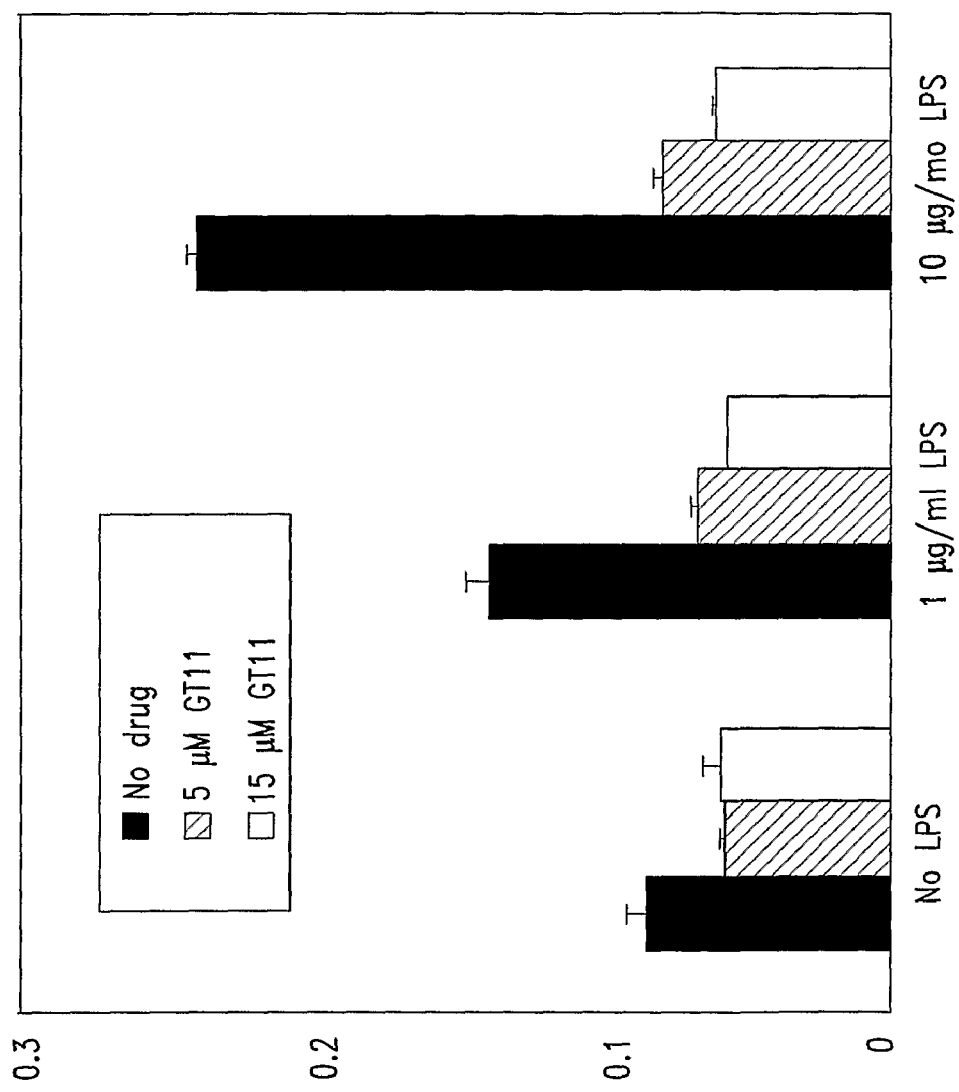
FIG. 5 shows the effects of the SPL inhibitor GT11 (C8-cyclopropenylceramide, Matreya LLC, Pleasant Gap, Pa., catalogue number 1886) on LPS-stimulated proliferation of C3H murine splenocytes and thymocytes in vitro.

Mitogen Induced Lymphoproliferation—LPS-stimulated cellular proliferation under conditions described above in Example 1 was quantified using two different dosages of an SPL inhibitor, GT111 (C8 analogue) and the results are depicted in FIG. 5. Lymphoproliferation was reduced in the presence of the SPL inhibitor. Examination by light microscopy of samples of cells recovered from control and experimental cell cultures indicated that non-specific cytotoxic effects of GT11 were negligible.

ADDITIONAL PUBLICATIONS CITED

1. Budde, K., Schmouder, R., Brunkhorst, R., Nashan, B., Lucker, P., Mayer, T., Choudhury, S., Skerjanec, A., G, K., and Neumayer, H. (2002) *J Am Soc Nephrol* 13, 1073-1083
2. Brinkmann, V. (2004) *Yonsei Med J* 45, 991-997
3. Brinkmann, V., and Lynch, K. R. (2002) *Curr Opin Immunol* 14, 569-575
4. Chiba, K., Yanagawa, Y., Masubuchi, Y., Kataoka, H., Kawaguchi, T., and Ohtsuki, M. (1998) *J Immunol* 160, 5037-5044
5. Matloubian, M., Lo, C. G., Cinamon, G., Lesneski, M. J., Xu, Y., Brinkmann, V., Allende, M. L., Proia, R. L., and Cyster, J. G. (2004) *Nature* 427, 355-360.
6. Mandala, S., Hajdu, R., Bergstrom, J., Quackenbush, E., Xie, J., Milligan, J., Thornton, R., Shei, G. J., Card, D., Keohane, C., Rosenbach, M., Hale, J., Lynch, C. L., Rupprecht, K., Parsons, W., and Rosen, H. (2002) *Science* 296, 346-349.
7. Xie, J. H., Nomura, N., Koprak, S. L., Quackenbush, E. J., Forrest, M. J., and Rosen, H. (2003) *J Immunol* 170, 3662-3670
8. Vora, K., Nichols, E., Porter, G., Cui, Y., Keohane, C., Hadju R, Hale, J., Neway, W., Zaller, D., and Mandala, S. (2005) *J Leukocyte Biology* 78, 1-10
9. Honig, S. M., Fu, S., Mao, X., Yopp, A., Gunn, M. D., Randolph, G. J., and Bromberg, J. S. (2003) *J Clin Invest* 111, 627-637
10. Sanchez, T., Estrada-Hernandez, T., Paik, J. H., Wu, M. T., Venkataraman, K., Brinkmann, V., Claffey, K., and Hla, T. (2003) *J Biol Chem* 278, 47281-47290
11. Kimura, T., Boehmler, A. M., Seitz, G., Kuci, S., Wiesner, T., Brinkmann, V., Kanz, L., and Mohle, R. (2004) *Blood*
12. Halin, C., Scimone, M., Bonasio, R., Gauguet, J., Mempel, T., Quackenbush, E., Proia, R., Mandala, S., and UH, v. A. (2005) *Blood* (ahead of print)
13. Pinschewer, D., Ochsenbein, A., Odermatt, B., and Brinkmann, V. (2000) *J Immunol* 164, 5761-5770
14. Fujita, T., Inoue, K., Yamamoto, S., Ikumoto, T., Sasaki, S., Toyama, R., Chiba, K., Hoshino, Y., and T, O. (1994) *J Antibiot* (Tokyo) 47, 208-215
15. Billich, A., Bornancin, F., Devay, P., Mechtcheriakova, D., Urtz, N., and Baumruker, T. (2003) *J Biol Chem* 278, 47408-47415
16. Brinkmann, V., Davis, M. D., Heise, C. E., Albert, R., Cottens, S., Hof, R., Bruns, C., Prieschl, E., Baumruker, T., Hiestand, P., Foster, C. A., Zollinger, M., and Lynch, K. R. (2002) *J Biol Chem* 277, 21453-21457
17. Allende, M. L., Dreier, J. L., Mandala, S., and Proia, R. L. (2004) *J Biol Chem* 279, 15396-15401
18. Graler, M. H., and Goetzl, E. J. (2004) *Faseb J* 18, 551-553
19. Spiegel, S., and Milstien, S. (2000) *FEBS Lett* 476, 55-57
20. Reiss, U., Oskouian, B., Zhou, J., Gupta, V., Sooriyakumaran, P., Kelly, S., Wang, E., Merrill, A. H., Jr., and Saba, J. D. (2004) *J Biol Chem* 279, 1281-1290
21. Van Veldhoven, P. P., and Mannaerts, G. P. (1991) *J Biol Chem* 266, 12502-12507
22. Jiang, Q., Wong, J., Fyrst, H., Saba, J., and Ames, B. (2004) *Proc Natl Acad Sci USA* 101, 17825-17830
23. Fyrst, H., Herr, D. R., Harris, G. L., and Saba, J. D. (2004) *J Lipid Res* 45, 54-62
24. Caligan, T. B., Peters, K., Ou, J., Wang, E., Saba, J., and Merrill, A. H., Jr. (2000) *Anal. Biochem.* 281, 36-44
25. Oskouian, B., Mendel, J., Shocron, E., Lee, M. A., Jr., Fyrst, H., and Saba, J. D. (2005) *J Biol Chem* 280, 18403-18410
26. Mishell, B., Shiigi, S., Henry, C., Chan, E., North, J., Gallily, R., Slomich, M., Miller, K., Marbrook, J., Parks, D., and Good, A. (1980) in *Selected Methods in Cellular Immunology* (Mishell, B., and Shiigi, S., eds), pp. 3-27, WH Freeman and Company, San Francisco
27. Triola, G., Fabrias, G., Dragusin, M., Niederhausen, L., Broere, R., Llebaria, A., and van Echten-Deckert, G. (2004) *Mol Pharmacol* 66, 1671-1678

28. Scountzou, J., Malisiovas, N., Antoniadis, A., and Trakatellis, A. (1989) *Immunopharmacol Immunotoxicol* 11, 657-666
29. Campbell, R., Kurtz, G., and Norton-Reel, D. (1991) *Life Sci* 48, 225-235
30. Mendel, J., Heinecke, K., Fyrst, H., and Saba, J. D. (2003) *J Biol Chem* 278, 22341-22349
31. Herr, D. R., Fyrst, H., Phan, V., Heinecke, K., Georges, R., Harris, G. L., and Saba, J. D. (2003) *Development* 130, 2443-2453
32. Li, G., Foote, C., Alexander, S., and Alexander, H. (2001) *Development* 128, 3473-3483.
33. Brinkmann, V., and Lynch, K. R. (2002) *Curr Opin Immunol* 14, 569-575
34. Graler, M. H., and Goetzl, E. J. (2004) *Faseb J* 18, 551-553
35. Honig, S. M., Fu, S., Mao, X., Yopp, A., Gunn, M. D., Randolph, G. J., and Bromberg, J. S. (2003) *J Clin Invest* 111, 627-637
36. Billich, A., Bornancin, F., Devay, P., Mechtcheriakova, D., Urtz, N., and Baumruker, T. (2003) *J Biol Chem* 278, 47408-47415
37. Kimura, T., Boehmler, A. M., Seitz, G., Kuci, S., Wiesner, T., Brinkmann, V., Kanz, L., and Mohle, R. (2004) *Blood*
38. Brinkmann, V., Davis, M. D., Heise, C. E., Albert, R., Cottens, S., Hof, R., Bruns, C., Prieschl, E., Baumruker, T., Hiestand, P., Foster, C. A., Zollinger, M., and Lynch, K. R. (2002) *J Biol Chem* 277, 21453-21457
39. Tedesco-Silva, H., Mourad, G., Kahan, B., Boira, J., Weimar, W., Mulgaonkar, S., Nashan, B., Madsen, S., Charpentier, B., Pellet, P., and Vanrenterghem, Y. (2004) *Transplantation* 77, 1826-1833
40. Chiba, K., Hoshino, Y., Ohtsuki, M., Kataoka, H., Maeda, Y., Matsuyuki, H., Sugahara, K., Kiuchi, M., Hirose, R., and Adachi, K. (2005) *Transplant Proc* 37, 102-106
41. Galvao, V. R., Ginoza, M., Franco, M., Burdmann, E. A., and Bueno, V. (2005) *Transplant Proc* 37, 112-113
42. Kataoka, H., Ohtsuki, M., Shimano, K., Mochizuki, S., Oshita, K., Murata, M., Sugahara, K., Sato, N., Hoshino, Y., and Chiba, K. (2005) *Transplant Proc* 37, 107-109
43. Schmid, G., Guba, M., Papyan, A., Ischenko, I., Bruckel, M., Bruns, C. J., Jauch, K. W., and Graeb, C. (2005) *Transplant Proc* 37, 110-111
44. Yan, S., Rodriguez-Barbosa, J. I., Pabst, O., Beckmann, J. H., Brinkmann, V., Forster, R., and Hoffmann, M. W. (2005) *Transplant Proc* 37, 114-115
45. Vora, K., Nichols, E., Porter, G., Cui, Y., Keohane, C., Hadju R, Hale, J., Neway, W., Zaller, D., and Mandala, S. (2005) *J Leukocyte Biology* 78, 1-10
46. Halin, C., Scimone, M., Bonasio, R., Gauguet, J., Mempel, T., Quackenbush, E., Proia, R., Mandala, S., and UH, v. A. (2005) *Blood* (ahead of print)
47. Brinkmann, V. (2004) *Yonsei Med J* 45, 991-997
48. Pinschewer, D., Ochsenbein, A., Odermatt, B., and Brinkmann, V. (2000) *J Immunol* 164, 5761-5770
49. Budde, K., Schmouder, R., Brunkhorst, R., Nashan, B., Lucker, P., Mayer, T., Choudhury, S., Skerjanec, A., G, K., and Neumayer, H. (2002) *J Am Soc Nephrol* 13, 1073-1083
50. Chiba, K., Yanagawa, Y., Masubuchi, Y., Kataoka, H., Kawaguchi, T., and Ohtsuki, M. (1998) *J Immunol* 160, 5037-5044
51. Mandala, S., Hajdu, R., Bergstrom, J., Quackenbush, E., Xie, J., Milligan, J., Thornton, R., Shei, G. J., Card, D., Keohane, C., Rosenbach, M., Hale, J., Lynch, C. L., Rupprecht, K., Parsons, W., and Rosen, H. (2002) *Science* 296, 346-349.
52. Xie, J. H., Nomura, N., Koprak, S. L., Quackenbush, E. J., Forrest, M. J., and Rosen, H. (2003) *J Immunol* 170, 3662-3670
53. Matloubian, M., Lo, C. G., Cinamon, G., Lesneski, M. J., Xu, Y., Brinkmann, V., Allende, M. L., Proia, R. L., and Cyster, J. G. (2004) *Nature* 427, 355-360
54. Forrest, M., Sun, S. Y., Hajdu, R., Bergstrom, J., Card, D., Doherty, G., Hale, J., Keohane, C., Meyers, C., Milligan, J., Mills, S., Nomura, N., Rosen, H., Rosenbach, M., Shei, G. J., Singer, II, Tian, M., West, S., White, V., Xie, J., Proia, R. L., and Mandala, S. (2004) *J Pharmacol Exp Ther* 309, 758-768
55. Frydas, S., Papaioannou, N., Reale, M., Barbacane, R., and Conti, P. (2002) *Immunol Lett,* 31-37
56. Scountzou, J., Malisiovas, N., Antoniadis, A., and Trakatellis, A. (1989) *Immunopharmacol Immunotoxicol* 11, 657-666
57. Campbell, R., Kurtz, G., and Norton-Reel, D. (1991) *Life Sci* 48, 225-235

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

---

What is claimed is:

1. A method of suppressing immune function in a subject, comprising administering to the subject an agent that inhibits sphingosine-1-phosphate lyase (SPL) activity, thereby suppressing immune function wherein the agent that alters sphinosine-1-phosphate lysate (SPL) activity is selected from the group consisting of deoxypyridoxine, $C_8$-cyclopropenylceramide and $C_{16}$-cyclopropenylceramide.

2. The method of claim 1 wherein suppressing immune function comprises reducing tissue inflammation in the subject.

3. The method of claim 1 wherein suppressing immune function comprises treating a condition that is selected from the group consisting of transplant graft rejection, autoimmune disease and allergy.

4. The method of claim 1 wherein suppressing immune function comprises reducing proliferation or survival of an immune system cell.

5. The method of claim 4 wherein the immune system cell is a lymphocyte or a hematopoietic cell of lymphoid lineage.

6. The method of claim 1 wherein the agent that is capable of decreasing SPL activity binds to SPL.

7. The method of claim 1 wherein the agent that alters sphingosine-1-phosphate lyase (SPL) activity is not FTY720 or myriocin.

* * * * *

UNITED STATES PATENT AND TRADEMARK OFFICE
CERTIFICATE OF CORRECTION

PATENT NO. : 8,124,111 B2
APPLICATION NO. : 11/917029
DATED : February 28, 2012
INVENTOR(S) : Julie D. Saba It is certified that error appears in the above-identified patent and that said Letters Patent is hereby corrected as shown below:

Item (56):
"Jiang et al., "γ-Tocopherol or combinations of vitamin E forms induce cell death in human prostate cancer cells by interrupting sphingolipid synthesis," *PNAS 101*(50:17825-17830, 2004." should read, --Jiang et al., "γ-Tocopherol or combinations of vitamin E forms induce cell death in human prostate cancer cells by interrupting sphingolipid synthesis," *PNAS 101*(51):17825-17830, 2004.--.

Item (56):
"Togias, "Unique mechanistic features of allergic rhinitis," *Journal of Allergy and Clinical Immunology 105*(6 part 2):S599-5604, June 2000." should read, --Togias, "Unique mechanistic features of allergic rhinitis," *Journal of Allergy and Clinical Immunology 105*(6 part 2):S599-S604, June 2000.--.

Item (56):
"Triola et al., "Specificity of the dihydroceramide desaturase inhibitor *N*-[(1*R*,2*S*)-2-hydroxy-1-hydroxymethyl-2-(2-tridecyl-1-cyclopropenylethyl]octanamide (GT11) in primary cultured cerebellar neurons," *Molecular Pharmacology 66*(6):1671-1678, 2004." should read, --Triola et al., "Specificity of the dihydroceramide desaturase inhibitor *N*-[(1*R*,2*S*)-2-hydroxy-1-hydroxymethyl-2-(2-tridecyl-1-cyclopropenyl)ethyl]octanamide (GT11) in primary cultured cerebellar neurons," *Molecular Pharmacology 66*(6):1671-1678, 2004.--.

Signed and Sealed this
Eleventh Day of September, 2012

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 8,124,111 B2 | Page 1 of 1 |
| APPLICATION NO. | : 11/917029 | |
| DATED | : February 28, 2012 | |
| INVENTOR(S) | : Julie D. Saba | |

It is certified that error appears in the above-identified patent and that said Letters Patent is hereby corrected as shown below:

In the Specification

Column 1, Lines 7-10:
"This invention was made with government support under Grant No. CA77528 awarded by the National Institutes of Health. The government may have certain rights in this invention." should read, --This invention was made with government support under Grant No. CA77528 awarded by the National Institutes of Health. The government has certain rights in this invention.--.

Signed and Sealed this
Twenty-second Day of July, 2014

Michelle K. Lee
*Deputy Director of the United States Patent and Trademark Office*